United States Patent
Kawamura et al.

Patent Number: 6,074,734
Date of Patent: Jun. 13, 2000

[54] ORGANIC ELECTROLUMINESCENCE DEVICE, ORGANIC THIN FILM, AND TRIAMINE COMPOUND

[75] Inventors: Hisayuki Kawamura; Hiroaki Nakamura; Chishio Hosokawa, all of Sodegaura, Japan

[73] Assignee: Idemitsu Kosan Co., Ltd., Tokyo, Japan

[21] Appl. No.: 08/860,927

[22] PCT Filed: Jan. 19, 1996

[86] PCT No.: PCT/JP96/00082

§ 371 Date: Jul. 21, 1997

§ 102(e) Date: Jul. 21, 1997

[87] PCT Pub. No.: WO96/22273

PCT Pub. Date: Jul. 25, 1996

[30] Foreign Application Priority Data

Jan. 19, 1995 [JP] Japan .................................. 7-006254
Sep. 29, 1995 [JP] Japan .................................. 7-252979

[51] Int. Cl.[7] .................. B23B 7/02; C07C 211/00; H01J 1/62
[52] U.S. Cl. .................. 428/220; 564/307; 564/429; 564/433; 564/434; 313/503; 313/504; 313/506; 313/509
[58] Field of Search .................. 40/544; 564/307, 564/429, 433, 434; 428/220, DIG. 917; 313/503, 504, 506, 509

[56] References Cited

FOREIGN PATENT DOCUMENTS

| 562883 A2 | 9/1993 | European Pat. Off. . |
|---|---|---|
| 0 779 765 | 6/1997 | European Pat. Off. . |
| 03064760 A2 | 3/1993 | Japan . |
| 05224440 A2 | 9/1993 | Japan . |
| 08031574 A2 | 2/1996 | Japan . |
| 08109373 A2 | 4/1996 | Japan . |
| 08185982 A2 | 7/1996 | Japan . |
| 08199163 A2 | 8/1996 | Japan . |

OTHER PUBLICATIONS

Yasuhiko Shirota, et al., Applied Physics Letters, vol. 65, No. 7, pp. 807–809, "Multilayered Organic Electroluminescent Device Using a Novel Starburst Molecule, 4,4',4"–Tris (3–Methylphenylphenylamino) Triphenylamine, as a Hole Transport Material", 1994.

*Primary Examiner*—Jose' G. Dees
*Assistant Examiner*—Alton Pryor
*Attorney, Agent, or Firm*—Oblon, Spivak, McClelland, Maier & Neustadt, P.C.

[57] ABSTRACT

The present invention provides a triamine compound represented by general formula (I):

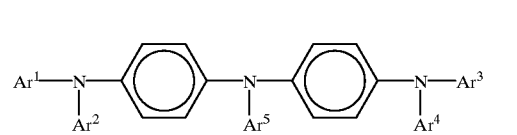

an organic luminescence device which comprises an organic layer and a pair of electrodes disposed on both sides of the organic layer wherein the organic layer at least contains a layer of a light emitting zone and a layer of a hole transporting zone which comprises a hole injecting layer containing the triamine compound and a hole transporting layer, and an organic thin film comprising two layers which are a layer containing a compound represented by general formula (I) and having a thickness of 5 nm to 5 μm and a layer containing a compound represented by general formula (II):

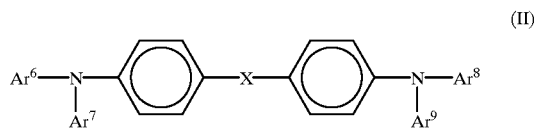

10 Claims, 2 Drawing Sheets

ORGANIC ELECTROLUMINESCENCE DEVICE, ORGANIC THIN FILM, AND TRIAMINE COMPOUND

TECHNICAL FIELD

This application is a 371 of PCT/JP 96/00082 filed Jan. 19, 1996.

The present invention relates to an organic electroluminescence device, an organic thin film, and a triamine compound. More particularly, the present invention relates to an organic electroluminescence device which has little possibility of dielectric breakdown after storage for a long time and shows a remarkably increased efficiency of light emission because a specific triamine is used in the hole injecting layer, an organic thin film which shows very excellent hole injecting and transporting properties and is advantageously used for the organic electroluminescence device and photosensitive films in the electronic photography, and a triamine compound which provides an organic electroluminescence device having a long life and showing an excellent stability of light emission when the triamine compound is used for the device.

BACKGROUND ART

Electroluminescence devices which utilize the electroluminescence show high self-distinguishability because of the self-emission and are excellent in impact resistance because they are completely solid devices. Therefore, electroluminescence devices have been attracting attention for application as light emitting devices in various types of display apparatus.

The electroluminescence devices include inorganic electroluminescence devices in which an inorganic compound is used as the light emitting material, and organic electroluminescence devices in which an organic compound is used as the light emitting material. Organic electroluminescence devices have been extensively studied for practical application as a display device of the next generation because the applied voltage can be decreased to a large extent.

As for the construction of the organic electroluminescence device, the basic construction comprises an anode/a light emitting layer/a cathode. (This description shows that an anode, a light emitting layer, and a cathode are laminated in this order. Other constructions are described in the same manner.) Constructions having a hole injecting and transporting layer or an electron injecting and transporting layer suitably added to the basic construction are known. Examples of such construction include the construction of an anode/a hole injecting and transporting layer/a light emitting layer/a cathode and the construction of an anode/a hole injecting and transporting layer/a light emitting layer/an electron injecting and transporting layer/a cathode. The hole injecting and transporting layer has the function of transporting holes injected from the anode to the light emitting layer. The electron injecting and transporting layer has the function of transporting electrons injected from the cathode to the light emitting layer. It has been known that, when the hole injecting and transporting layer is inserted between the light emitting layer and the anode, more holes are injected into the light emitting layer in a lower electric field, and electrons injected into the light emitting layer from the cathode or the electron injecting and transporting layer are accumulated at the interface between the hole injecting and transporting layer and the light emitting layer because the hole injecting and transporting layer does not transport electrons. As the result, efficiency of the light emission is increased.

Organic electroluminescence devices have a problem that, because an ultra-thin film made of an organic compound is used in organic electroluminescence devices, the thin film is crystallized to cause dielectric breakdown after storage of the devices for a long time.

Heretofore, in organic electroluminescence devices, a phthalocyanine material is generally used at the interface with an anode as the hole injecting material. The phthalocyanine material is a particularly easily crystallizable material among organic materials used in electroluminescence devices, and development of a hole injecting material which can replace the phthalocyanine material and shows a high degree of amorphous property has been desired.

To solve the above problem, a technology using an amine of the dendrimer type as the hole injecting material which can suppress the dielectric breakdown in the device has been proposed (the specification of Japanese Patent Application Laid-Open No. Heisei 4(1992)-308688). However, this technology has a problem that the efficiency of light emission of the obtained device is low. A technology using an organic semiconductor of the oligomer type as the hole injecting material has also been disclosed (the specification of European Patent No. 439627). However, this technology is not suitable for practical application either because the efficiency of light emission of the obtained device is low.

Moreover, the above organic electric luminescence devices have a problem that the luminance of the light emission is decreased after the devices have been driven continuously for a long time, and this problem is another major obstacle for practical use of these devices.

In order to solve the above problems, a technology has been disclosed in which the generation of the leak current is prevented by using an amine of the dendrimer type, and the light emission can be maintained for a long time with stability (the specification of Japanese Patent Application Laid-Open No. Heisei 4(1992)-308688).

However, although this technology is effective for preventing the short-circuit, the stability of light emission is still insufficient for the practical application.

Accordingly, the present invention has an object of providing an organic electroluminescence device which has little possibility of dielectric breakdown after storage for a long time and shows a remarkably increased efficiency of light emission by using a material which is not easily crystallized as the hole injecting material, and an organic thin film which shows very excellent hole injecting and transporting properties and is advantageously used for the organic electroluminescence device and photosensitive films in the electronic photography.

The present invention has another object of providing a novel compound which provides an organic electroluminescence device having a long life and showing an excellent stability of light emission when the novel compound is used for the device.

DISCLOSURE OF THE INVENTION

As the result of extensive studies to achieve the first object of the present invention described above, it was found that an organic electroluminescence device in which a specific triamine is used as the hole injecting material has little possibility of dielectric breakdown even after storage for a long time and shows a remarkably high efficiency of light emission. It was also found that an organic thin layer comprising two layers which are a layer containing the specific triamine compound and having a specific thickness and a layer containing a specific compound and having a specific thickness exhibits very excellent hole injecting and transporting properties.

It was also found by the present inventors that a novel triamine having a specific structure containing an aryl group is advantageously used for achieving the second object of the present invention described above.

The present invention has been completed on the basis of the above discoveries.

Accordingly the present invention provides an organic electroluminescence device which comprises an organic layer at least comprising a layer of a hole transporting zone and a layer of a light emitting zone and a pair of electrodes disposed on both sides of the organic layer, wherein the layer of a hole transporting zone at least comprises a hole injecting layer and a hole transporting layer, and the hole injecting layer contains a compound represented by general formula (I):

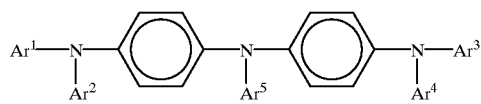

(I)

[wherein $Ar^1$ to $Ar^5$ represent each an aryl group having 6 to 18 core carbon atoms which is unsubstituted or substituted with an alkyl group, an alkoxy group, vinyl group, or styryl group, and may be the same with each other or different from each other (the number of core carbon atom means the number of carbon atom forming an aromatic ring among the carbon atoms of the aryl group)] and is in contact with an anode. $Ar^1$ to $Ar^5$ in general formula (I) preferably represent each an aryl group having 6 to 18 carbon atoms which is unsubstituted or substituted with an alkyl group, an alkoxy group, vinyl group, or styryl group.

In the present invention, it is preferred that the hole transporting layer in the electroluminescence device contains a compound represented by general formula (II):

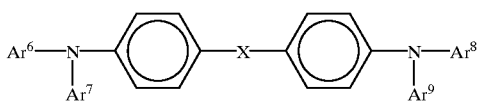

(II)

[wherein X represents a single bond, methylene group, phenylene group, biphenylene group, —O—, —S—, or a group represented by any of:

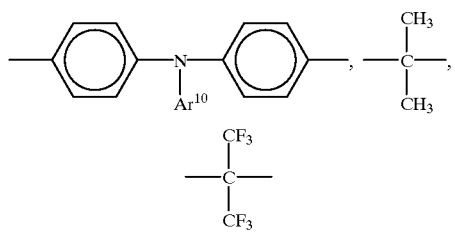

and $Ar^6$ to $Ar^{10}$ represent each an aryl group having 6 to 18 carbon atoms which is unsubstituted or substituted with an alkyl group, an alkoxy group, vinyl group, or styryl group, and may be the same with each other or different from each other].

The present invention also provides an organic thin film comprising two layers which are a layer containing a compound represented by general formula (I) and having a thickness of 5 nm to 5 μm and a layer containing a compound represented by general formula (II) and having a thickness of 5 nm to 5 μm.

The present invention further provides a triamine compound represented by general formula (III):

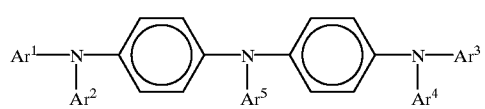

(III)

[wherein $Ar^1$ to $Ar^4$ represent each an aryl group having 6 to 18 core carbon atoms which is unsubstituted or substituted with an alkyl group, an alkoxy group, vinyl group, or styryl group and may be the same with each other or different from each other, and $Ar^5$ represents biphenyl group which is unsubstituted or substituted]. In this triamine compound, it is preferred that $Ar^5$ in general formula (III) represents an aryl group represented by:

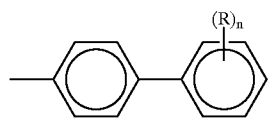

[wherein R represents hydrogen, an alkyl group having 1 to 6 carbon atoms, an alkoxy group having 1 to 6 carbon atoms, or phenyl group, n represents an integer of 0 to 5, and when a plurality of R are present, the plurality of R may be the same with each other or different from each other], and $Ar^1$ to $Ar^4$ represent each an aryl group represented by any of:

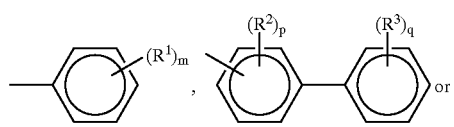

-continued

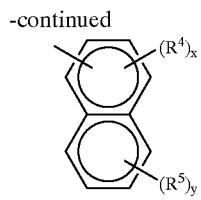

[wherein R¹ to R⁵ represent each hydrogen, an alkyl group having 1 to 6 carbon atoms, an alkoxy group having 1 to 6 carbon atoms, or phenyl group, m represents an integer of 0 to 5, p represents an integer of 0 to 4, q represents an integer of 0 to 5, x represents an integer of 0 to 3, y represents an integer of 0 to 4, and when a plurality of R¹, R², R³, R⁴, or R⁵ are present, the plurality of R¹, R², R³, R⁴, or R⁵ may be the same with each other or different from each other].

THE MOST PREFERRED EMBODIMENT TO CARRY OUT THE INVENTION

Figure 1:
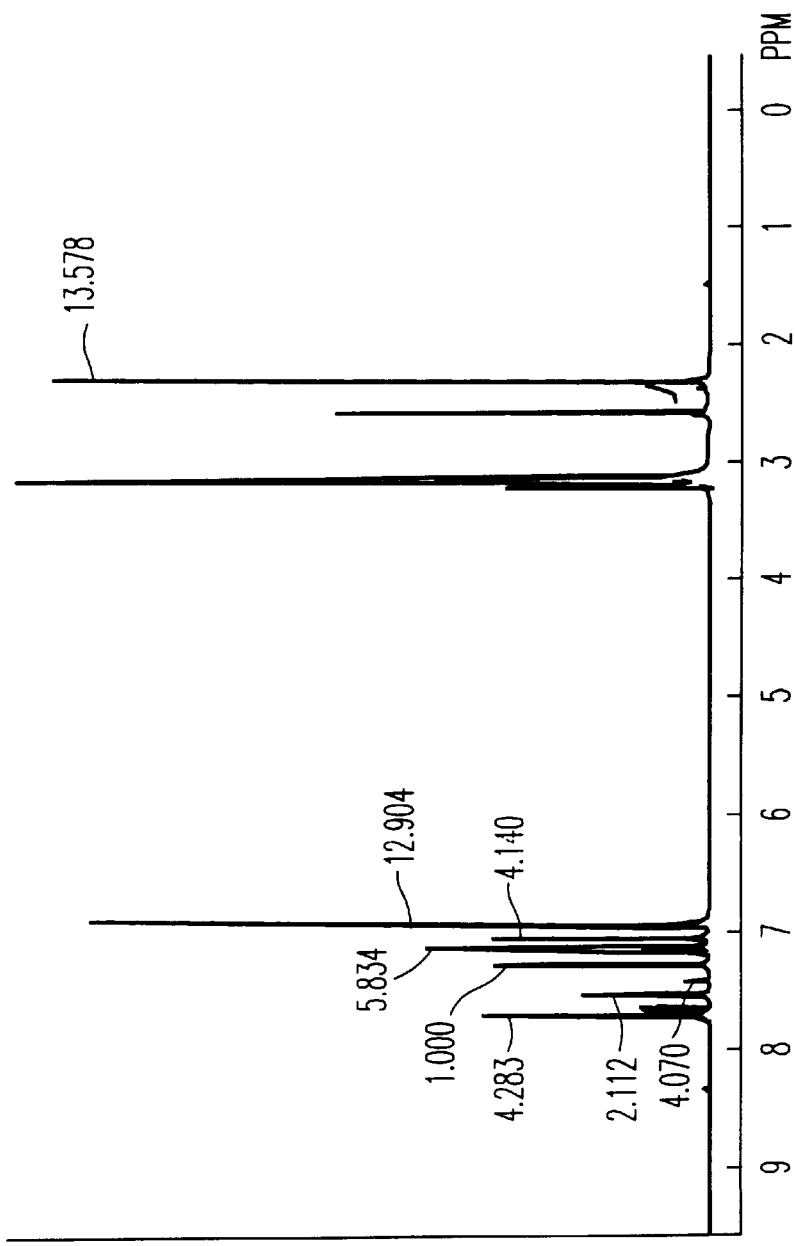
FIG. 1 shows a whole chart of the $^1$H-NMR spectrum of 4,4'-bis[N,N-di-(3-tolyl)amino]-4"-phenyl-triphenylamine obtained in Example 9.

The organic electroluminescence device of the present invention comprises an organic layer at least comprising a layer of a hole transporting zone and a layer of a light emitting zone, and a pair of electrodes, i.e., an anode and a cathode, disposed on both sides of the organic layer.

The anode in this electroluminescence device is an electrode used for injecting holes into the device. As the anode, an electrode made of a material, such as a metal, an alloy, an electrically conductive compound, and a mixture of these compounds, which has a large work function (4 eV or more) is preferably used. Specific examples of the material for the anode include metals, such as Au, and dielectric transparent materials, such as CuI, ITO, SnO$_2$, and ZnO. The anode can be prepared by forming a thin film of the material described above by a method, such as the vapor deposition and the sputtering. When the light is obtained through the anode, it is preferred that the transmittance of the anode is larger than 10%. It is also preferred that the electric resistance of the sheet as the anode is several hundred Ω/□ or less.

The thickness of the anode is selected generally in the range of 500 nm or less, preferably in the range of 10 to 200 nm, although the thickness depends on the used material.

On the other hand, the cathode is an electrode used for injecting electrons into the device. As the cathode, an electrode made of a material, such as a metal, an alloy, an electric conductive compound, or a mixture of these compounds, which has a small work function (4 eV or less) is used. Specific examples of the material for the cathode include sodium, sodium-potassium alloys, magnesium, aluminum, lithium, magnesium/copper mixtures, aluminum-lithium alloys, Al/Al$_2$O$_3$ mixtures, indium, and ytterbium. The cathode can be prepared by forming a thin film of the material described above by a method, such as the vapor deposition and the sputtering. When the light is obtained through the cathode, it is preferred that the transmittance of the cathode is larger than 10%. It is also preferred that the electric resistance of the sheet as the cathode is several hundred Ω/□ or less. The thickness of the cathode is selected generally in the range of 500 nm or less, preferably in the range of 10 to 200 nm, although the thickness depends on the used material.

In the device of the present invention, it is preferred that at least one of the anode and the cathode is formed with a transparent or semi-transparent material. It is enabled by using such a material that the light is efficiently transmitted and obtained.

In the organic electroluminescence device of the present invention, the hole transporting zone means a zone generally showing a mobility of holes of $10^{-6}$ cm$^2$/V.s or more when an electric field of $10^4$ to $10^6$ V/cm is applied. In the present invention, the layer of the hole transporting zone at least comprises a hole injecting layer and a hole transporting layer. It is necessary that the hole injecting layer contain a compound represented by general formula (I):

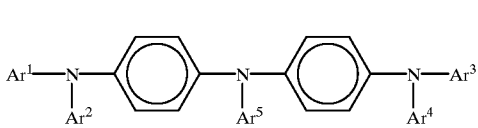

(I)

as the major component.

In above general formula (I), Ar$^1$ to Ar$^5$ represent each an aryl group having 6 to 18 core carbon atoms, preferably an aryl group having 6 to 18 carbon atoms, which is unsubstituted or substituted with an alkyl group, an alkoxy group, vinyl group, or styryl group, and may be the same with each other or different from each other. As the alkyl group and the alkoxy group, an alkyl group and an alkoxy group, respectively, having 1 to 6 carbon atoms are more preferable, and any of a linear, branched, and cyclic groups may be used. Examples of such an alkyl group and an alkoxy group include methyl group, ethyl group, n-propyl group, isopropyl group, n-butyl group, isobutyl group, sec-butyl group, t-butyl group, various types of pentyl group, various types of hexyl group, cyclopentyl group, cyclohexyl group, methoxy group, ethoxy group, n-propoxy group, isopropoxy group, n-butoxy group, isobutoxy group, sec-butoxy group, t-butoxy group, various types of pentoxy group, various types of hexoxy group, cyclopentoxy group, and cyclohexoxy group. When the aryl group having 6 to 18 core carbon atoms is substituted, a single substituent or a plurality of substituents may be introduced into the aromatic ring. The substituents may also be bonded together to form a ring. Examples of the aromatic ring in the aromatic group include benzene ring, naphthalene ring, acenaphthene ring, anthracene ring, fluorene ring, phenanthrene ring, pyrene ring, and biphenyl ring. Ar$^1$ to Ar$^5$ may be the same with each other or different from each other.

Specific examples of the above compound represented by general formula (I) are shown in Table 1.

TABLE 1-1A

| compound | Ar¹ | Ar² | Ar³ |
|---|---|---|---|
| HI-1 | –Ph | –Ph | –Ph |
| HI-2 | –C₆H₄–Me (p) | –C₆H₄–Me (p) | –C₆H₄–Me (p) |
| HI-3 | –C₆H₄–Me (m) | –C₆H₄–Me (m) | –C₆H₄–Me (m) |
| HI-4 | –C₆H₄–Me (o) | –C₆H₄–Me (o) | –C₆H₄–Me (o) |
| HI-5 | –C₆H₄–Et (p) | –C₆H₄–Et (p) | –C₆H₄–Et (p) |
| HI-6 | –C₆H₄–nPr (p) | –C₆H₄–nPr (p) | –C₆H₄–nPr (p) |
| HI-7 | –C₆H₄–iPr (p) | –C₆H₄–iPr (p) | –C₆H₄–iPr (p) |
| HI-8 | –C₆H₄–nBu (p) | –C₆H₄–nBu (p) | –C₆H₄–nBu (p) |

TABLE 1-1B

| compound | Ar⁴ | Ar⁵ |
|---|---|---|
| HI-1 | –Ph | –Ph |
| HI-2 | –C₆H₄–Me (p) | –Ph |
| HI-3 | –C₆H₄–Me (m) | –Ph |
| HI-4 | –C₆H₄–Me (o) | –Ph |
| HI-5 | –C₆H₄–Et (p) | –Ph |
| HI-6 | –C₆H₄–nPr (p) | –Ph |

TABLE 1-1B-continued

| compound | Ar⁴ | Ar⁵ |
|---|---|---|
| HI-7 | —⌬—iPr | —⌬ |
| HI-8 | —⌬—nBu | —⌬ |

TABLE 1-2B

| compound | Ar⁴ | Ar⁵ |
|---|---|---|
| HI-9 | —⌬—sBu | —⌬ |
| HI-10 | —⌬—tBu | —⌬ |

TABLE 1-2A

| compound | Ar¹ | Ar² | Ar³ |
|---|---|---|---|
| HI-9 | —⌬—sBu | —⌬—sBu | —⌬—sBu |
| HI-10 | —⌬—tBu | —⌬—tBu | —⌬—tBu |
| HI-11 | —⌬—nPe | —⌬—nPe | —⌬—nPe |
| HI-12 | —⌬—cyclopentyl | —⌬—cyclopentyl | —⌬—cyclopentyl |
| HI13 | —⌬—nHx | —⌬—nHx | —⌬—nHx |
| HI-14 | —⌬—cyclohexyl | —⌬—cyclohexyl | —⌬—cyclohexyl |
| HI-15 | —⌬(Me,Me) | —⌬(Me,Me) | —⌬(Me,Me) |
| HI-16 | —⌬—OMe | —⌬—OMe | —⌬—OMe |

TABLE 1-2B-continued
| compound | Ar⁴ | Ar⁵ |
|---|---|---|
| HI-11 |  | 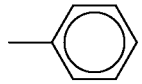 |
| HI-12 | 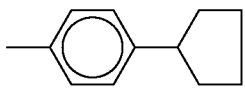 | 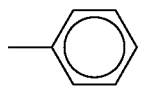 |
| HI-13 |  | 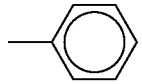 |
| HI-14 | 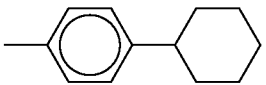 | 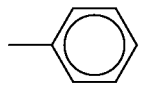 |
TABLE 1-2B-continued
| compound | Ar⁴ | Ar⁵ |
|---|---|---|
| HI-15 | 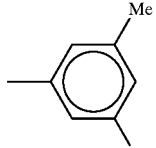 | 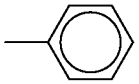 |
| HI-16 |  | 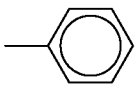 |
TABLE 1-3A
| compound | Ar¹ | Ar² | Ar³ |
|---|---|---|---|
| HI-17 |  |  | 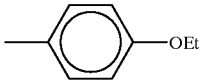 |
| HI-18 | 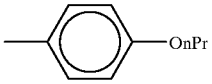 | 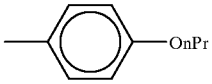 | 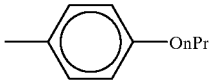 |
| HI-19 |  | 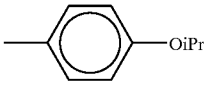 | 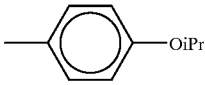 |
| HI-20 | 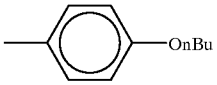 | 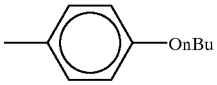 | 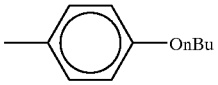 |
| HI-21 | 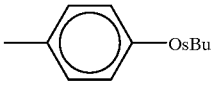 | 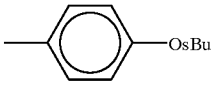 | 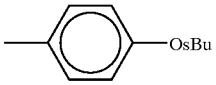 |
| HI-22 | 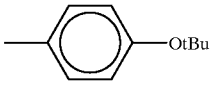 | 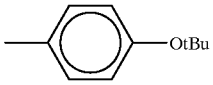 | 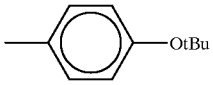 |
| HI-23 | 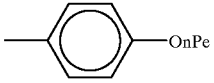 | 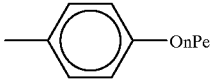 | 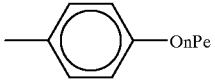 |

TABLE 1-3A-continued

| compound | Ar¹ | Ar² | Ar³ |
|---|---|---|---|
| HI-24 | —C₆H₄—OnHx | —C₆H₄—OnHx | —C₆H₄—OnHx |

TABLE 1-3B

| compound | Ar⁴ | Ar⁵ |
|---|---|---|
| HI-17 | —C₆H₄—OEt | —C₆H₅ |
| HI-18 | —C₆H₄—OnPr | —C₆H₅ |
| HI-19 | —C₆H₄—OiPr | —C₆H₅ |
| HI-20 | —C₆H₄—OnBu | —C₆H₅ |
| HI-21 | —C₆H₄—OsBu | —C₆H₅ |

TABLE 1-3B-continued

| compound | Ar⁴ | Ar⁵ |
|---|---|---|
| HI-22 | —C₆H₄—OtBu | —C₆H₅ |
| HI-23 | —C₆H₄—OnPe | —C₆H₅ |
| HI-24 | —C₆H₄—OnHx | —C₆H₅ |

TABLE 1-4A

| compound | Ar¹ | Ar² | Ar³ |
|---|---|---|---|
| HI-25 | —C₆H₄—CH=CH₂ | —C₆H₄—CH=CH₂ | —C₆H₄—CH=CH₂ |
| HI-26 | —C₆H₅ | —C₆H₅ | —C₆H₅ |
| HI-27 | —naphthyl | —naphthyl | —naphthyl |

TABLE 1-4A-continued

| compound | Ar¹ | Ar² | Ar³ |
|---|---|---|---|
| HI-28 | naphthyl | naphthyl | naphthyl |
| HI-29 | anthryl | anthryl | anthryl |
| HI-30 | phenanthryl | phenanthryl | phenanthryl |
| HI-31 | pyrenyl | pyrenyl | pyrenyl |

TABLE 1-4B

| compound | Ar⁴ | Ar⁵ |
|---|---|---|
| HI-25 | 4-vinylphenyl | phenyl |
| HI-26 | phenyl | 4-styrylphenyl |
| HI-27 | naphthyl | phenyl |

TABLE 1-4B-continued
| compound | Ar⁴ | Ar⁵ |
|---|---|---|
| HI-28 |  | 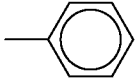 |
| HI-29 | 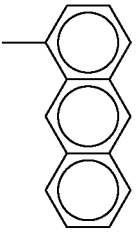 | 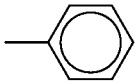 |
| HI-30 | 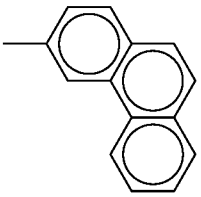 | 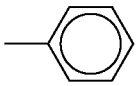 |
| HI-31 | 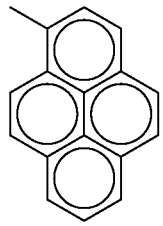 | 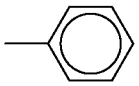 |
TABLE 1-5A
| compound | Ar¹ | Ar² | Ar³ |
|---|---|---|---|
| HI-32 | 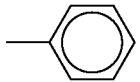 | 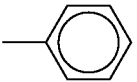 | 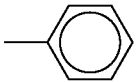 |
| HI-33 | 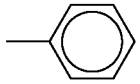 | 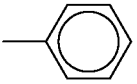 | 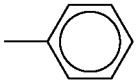 |
| HI-34 | 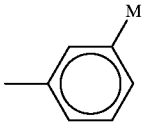 | 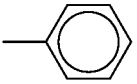 | 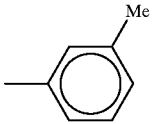 |
| HI-35 | 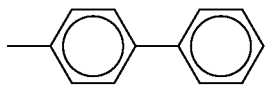 | 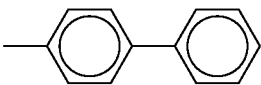 | 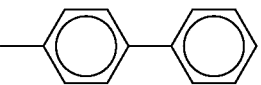 |

TABLE 1-5A-continued

| compound | Ar¹ | Ar² | Ar³ |
|---|---|---|---|
| HI-36 | 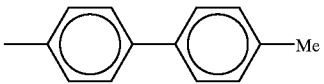 | 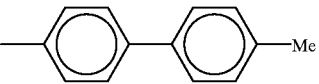 | 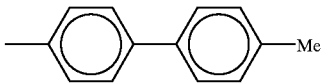 |
| HI-37 | 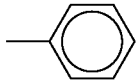 | 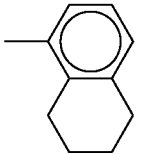 | 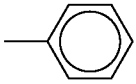 |

TABLE 1-5B

| compound | Ar⁴ | Ar⁵ |
|---|---|---|
| HI-32 | 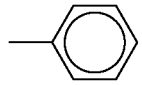 | 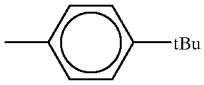 |
| HI-33 | 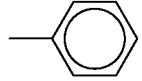 | 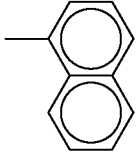 |
| HI-34 | 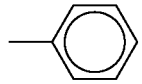 | 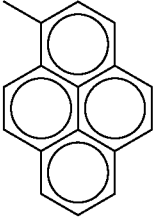 |
| HI-35 | 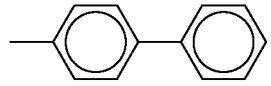 | 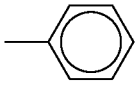 |
| HI-36 | 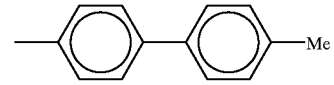 | 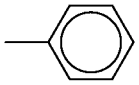 |
| HI-37 | 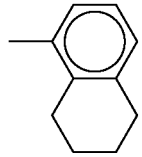 | 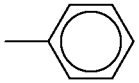 |

In the electroluminescence device of the present invention, the hole injecting layer may contain a single type or a combination of a plurality of types of the compound represented by general formula (I). It is necessary for achieving an efficient injection of holes that the hole injecting layer contain the compound represented by general formula (I), and it is also necessary that the hole injecting layer be disposed in contact with the anode. The thickness of the hole injecting layer is generally selected in the range of 5 nm to 5 μm.

On the other hand, the material used for the hole transporting layer in the electroluminescence device of the present invention is not particularly limited, and a material for a hole transporting layer which is generally used in electroluminescence devices can be used. Examples of the material for the hole transporting layer include triazole derivatives (such as those described in the specification of the U.S. Pat. No. 3,112,197), oxadiazole derivatives (such as those described in the specification of the U.S. Pat. No. 3,189,447), imidazole derivatives, polyarylalkane derivatives, pyrazoline derivatives, pyrazolone derivatives, phenylenediamine derivatives, arylamine derivatives, amino-substituted chalcone derivatives, oxazole derivatives, styrylanthracene derivatives, fluorenone derivatives, hydrazone derivatives, stilbene derivatives, silazane derivatives, polysilanes, aniline copolymers, and electrically conductive polymers (particularly, thiophene oligomers).

Aromatic tertiary-amine compounds and styrylamine compounds can also be used as the material for the hole transporting layer. Representative examples of such compounds include N,N,N',N'-tetraphneyl-4,4'-diaminophenyl, N,N'-diphenyl-N,N'-di(3-methylphenyl)-4,4'-diaminobiphenyl (TPDA), 2,2-bis(4-di-p-tolylaminophenyl) propane, 1,1-bis(4-di-p-tolylaminophenyl)cyclohexane, N,N,N',N'-tetra-p-tolyl-4,4'-diaminobiphenyl, 1,1-bis(4-di-p-tolylaminophenyl)-4-phenylcyclohexane, bis(4-dimethylamino-2-methylphenyl)phenylmethane, bis(4-di-p-tolylaminophenyl)phenylmethane, N,N'-diphenyl-N,N'-di(4-methoxyphenyl)-4,4'-diaminobiphenyl, N,N,N',N'-tetraphenyl-4,4'-diaminodiphenyl ether, 4,4'-bis(diphenylamino)terphenyl, N,N,N-tri(p-tolyl)amine, 4,4'-bis[4-(di-p-tolylamino)stilbene], 4-N,N-diphenylamino(2,2-diphenylvinyl)benzene, 3-methoxy-4'-N,N-diphenylaminostilbene, and N-phenylcarbazole.

In the present invention, it is particularly preferred that a layer containing a compound represented by general formula (II):

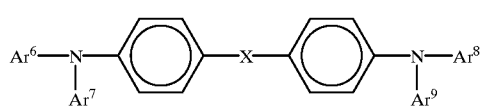

as the main component is used as the hole transporting layer. An organic electroluminescence device having a still higher efficiency of light emission can be obtained by using this layer.

In general formula (II), X represents a single bond, methylene group, phenylene group, biphenylene group, —O—, —S—, or a group represented by any of:

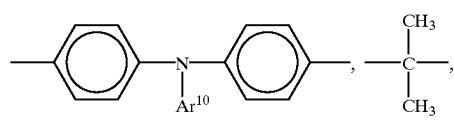

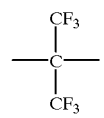

The positions in phenylene group or biphenylene group through which the phenylene group or the biphenylene group is bonded to the adjacent aromatic rings are not particularly limited. It is preferred that the phenylene group and the biphenylene group are 1,4-phenylene group and 4,4'-biphenylene group, respectively. $Ar^6$ to $Ar^{10}$ represent each an aryl group having 6 to 18 core carbon atoms, preferably an aryl group having 6 to 18 carbon atoms, which is unsubstituted or substituted with an alkyl group, an alkoxy group, vinyl group, or styryl group, i.e., the same aryl group as that represented by $Ar^1$ to $Ar^5$. $Ar^6$ to $Ar^{10}$ may be the same with each other or different from each other.

Specific examples of the compound represented by general formula (II) are shown in Table 2.

TABLE 2-1A

| compound | X | $Ar^6$ | $Ar^7$ |
|---|---|---|---|
| HT-1 | — | —⟨phenyl⟩—Me | —⟨phenyl⟩ |
| HT-2 | — | —⟨phenyl⟩—Et | —⟨phenyl⟩ |
| HT-3 | — | —⟨phenyl⟩—nPr | —⟨phenyl⟩ |
| HT-4 | — | —⟨phenyl⟩—iPr | —⟨phenyl⟩ |
| HT-5 | — | —⟨phenyl⟩—nBu | —⟨phenyl⟩ |
| HT-6 | — | —⟨phenyl⟩—sBu | —⟨phenyl⟩ |
| HT-7 | — | —⟨phenyl⟩—tBu | —⟨phenyl⟩ |
| HT-8 | — | —⟨phenyl⟩—nPe | —⟨phenyl⟩ |

TABLE 2-1B

| compound | Ar⁸ | Ar⁹ |
| --- | --- | --- |
| HT-1 | –C₆H₄–Me | –C₆H₅ |
| HT-2 | –C₆H₄–Et | –C₆H₅ |
| HT-3 | –C₆H₄–nPr | –C₆H₅ |
| HT-4 | –C₆H₄–iPr | –C₆H₅ |
| HT-5 | –C₆H₄–nBu | –C₆H₅ |
| HT-6 | –C₆H₄–sBu | –C₆H₅ |
| HT-7 | –C₆H₄–tBu | –C₆H₅ |
| HT-8 | –C₆H₄–nPe | –C₆H₅ |

TABLE 2-2A

| compound | X | Ar⁶ | Ar⁷ |
| --- | --- | --- | --- |
| HT-9 | — | –C₆H₄–(cyclopentyl) | –C₆H₅ |
| HT-10 | — | –C₆H₄–nHx | –C₆H₅ |
| HT-11 | — | –C₆H₄–(cyclohexyl) | –C₆H₅ |
| HT-12 | — | –C₆H₄–OMe | –C₆H₅ |
| HT-13 | — | –C₆H₄–OEt | –C₆H₅ |
| HT-14 | — | –C₆H₄–OnPr | –C₆H₅ |
| HT-15 | — | –C₆H₄–OiPr | –C₆H₅ |
| HT-16 | — | –C₆H₄–OnBu | –C₆H₅ |

TABLE 2-2B

| compound | Ar⁸ | Ar⁹ |
| --- | --- | --- |
| HT-9 | –C₆H₄–(cyclopentyl) | –C₆H₅ |
| HT-10 | –C₆H₄–nHx | –C₆H₅ |
| HT-11 | –C₆H₄–(cyclohexyl) | –C₆H₅ |
| HT-12 | –C₆H₄–OMe | –C₆H₅ |
| HT-13 | –C₆H₄–OEt | –C₆H₅ |
| HT-14 | –C₆H₄–OnPr | –C₆H₅ |
| HT-15 | –C₆H₄–OiPr | –C₆H₅ |

TABLE 2-2B-continued

| compound | Ar⁸ | Ar⁹ |
|---|---|---|
| HT-16 | —C₆H₄—OnBu | —C₆H₅ |

TABLE 2-3A

| compound | X | Ar⁶ | Ar⁷ |
|---|---|---|---|
| HT-17 | — | —C₆H₄—OsBu | —C₆H₅ |
| HT-18 | — | —C₆H₄—OtBu | —C₆H₅ |
| HT-19 | — | —C₆H₄—OnPe | —C₆H₅ |
| HT-20 | — | —C₆H₄—OnHx | —C₆H₅ |
| HT-21 | — | 3,5-dimethylphenyl (Me, Me) | —C₆H₅ |
| HT-22 | — | —C₆H₄—Me | —C₆H₄—Me |
| HT-23 | — | 3-methylphenyl (Me) | —C₆H₅ |

TABLE 2-3A-continued

| compound | X | Ar⁶ | Ar⁷ |
|---|---|---|---|
| HT-24 | — | 2-methylphenyl (Me) | —C₆H₅ |

TABLE 2-3B

| compound | Ar⁸ | Ar⁹ |
|---|---|---|
| HT-17 | —C₆H₄—OsBu | —C₆H₅ |
| HT-18 | —C₆H₄—OtBu | —C₆H₅ |
| HT-19 | —C₆H₄—OnPe | —C₆H₅ |
| HT-20 | —C₆H₄—OnHx | —C₆H₅ |
| HT-21 | 3,5-dimethylphenyl (Me, Me) | —C₆H₅ |
| HT-22 | —C₆H₄—Me | —C₆H₄—Me |
| HT-23 | 3-methylphenyl (Me) | —C₆H₅ |

TABLE 2-3B-continued
| compound | Ar⁸ | Ar⁹ |
|---|---|---|
| HT-24 | 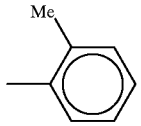 | 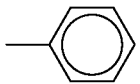 |
TABLE 2-4A
| compound | X | Ar⁶ | Ar⁷ |
|---|---|---|---|
| HT-25 | — | 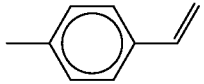 | 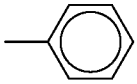 |
| HT-26 | — | 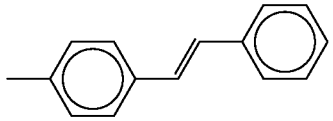 | 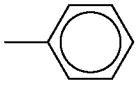 |
| HT-27 | — | 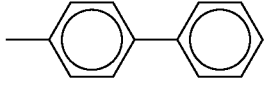 | 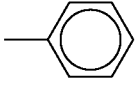 |
| HT-28 | — | 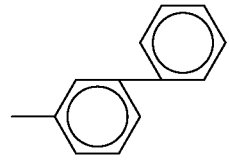 | 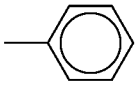 |
| HT-29 | — | 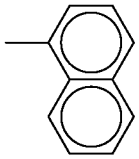 | 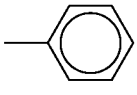 |
| HT-30 | — |  | 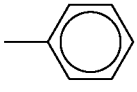 |
| HT-31 | — | 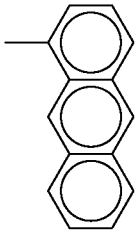 | 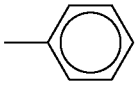 |

TABLE 2-4B
| compound | Ar⁸ | Ar⁹ |
| --- | --- | --- |
| HT-25 | 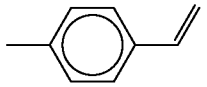 | 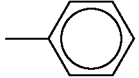 |
| HT-26 | 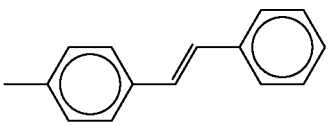 | 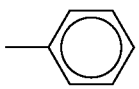 |
| HT-27 | 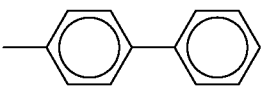 | 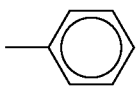 |
| HT-28 | 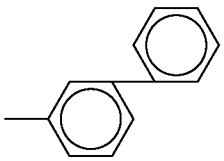 | 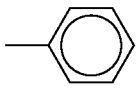 |
| HT-29 | 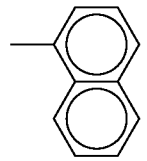 | 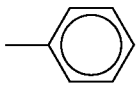 |
| HT-30 | 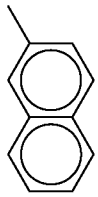 | 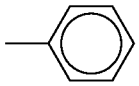 |
| HT-31 | 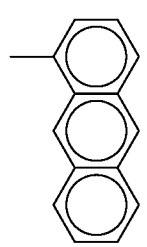 | 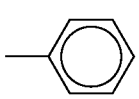 |

TABLE 2-5A
| compound | X | Ar⁶ | Ar⁷ |
|---|---|---|---|
| HT-32 | — | 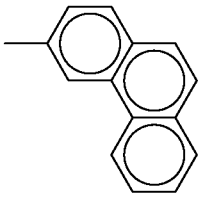 | 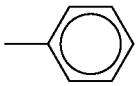 |
| HT-33 | — | 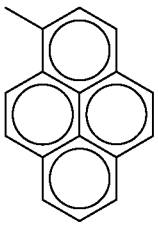 | 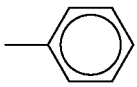 |
| HT-34 |  | 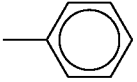 | 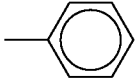 |
| HT-35 |  | 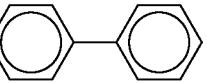 | 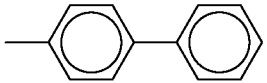 |
| HT-36 | —CH₂— |  | 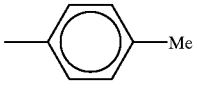 |
| HT-37 | —O— |  | 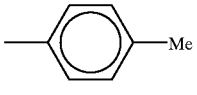 |
| HT-38 | —S— |  | 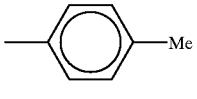 |
TABLE 2-5B
| compound | Ar⁸ | Ar⁹ |
|---|---|---|
| HT-32 | 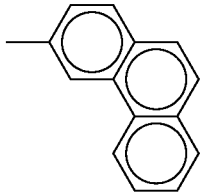 | 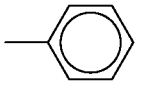 |

TABLE 2-5B-continued

| compound | Ar⁸ | Ar⁹ |
|---|---|---|
| HT-33 | pyrenyl (methyl-substituted) | phenyl |
| HT-34 | tolyl | phenyl |
| HT-35 | biphenyl | biphenyl |
| HT-36 | 4-methylphenyl | 4-methylphenyl |
| HT-37 | 4-methylphenyl | 4-methylphenyl |
| HT-38 | 4-methylphenyl | 4-methylphenyl |

TABLE 2-6A

| compound | X | Ar⁶ | Ar⁷ |
|---|---|---|---|
| HT-39 | 4,4'-(phenylimino)bis(phenylene) | phenyl | phenyl |
| HT-40 | 4,4'-(phenylimino)bis(phenylene) | 4-methylphenyl | 4-methylphenyl |
| HT-41 | 4,4'-(phenylimino)bis(phenylene) | biphenyl | biphenyl |

TABLE 2-6A-continued

| compound | X | Ar⁶ | Ar⁷ |
|---|---|---|---|
| HT-42 | 4-tBu-C₆H₄-N(4-MeC₆H₄)(4-MeC₆H₄)- (triarylamine with tBu on central phenyl) | phenyl | phenyl |
| HT-43 | 1-naphthyl-N(4-MeC₆H₄)(4-MeC₆H₄)- | phenyl | phenyl |
| HT-44 | -C(CH₃)₂- | phenyl | phenyl |
| HT-45 | -C(CF₃)₂- | phenyl | phenyl |

TABLE 2-6B

| compound | Ar⁸ | Ar⁹ |
|---|---|---|
| HT-39 | phenyl | phenyl |
| HT-40 | 4-Me-C₆H₄- | 4-Me-C₆H₄- |
| HT-41 | 4-biphenylyl | 4-biphenylyl |
| HT-42 | phenyl | phenyl |
| HT-43 | phenyl | phenyl |
| HT-44 | phenyl | phenyl |

TABLE 2-6B-continued

| compound | Ar⁸ | Ar⁹ |
| --- | --- | --- |
| HT-45 | 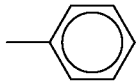 | 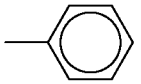 |

In the organic electroluminescence device of the present invention, the hole transporting layer may contain a single type or a combination of a plurality of types of the above compound. The thickness of the hole transporting layer is generally selected in the range of 5 nm to 5 $\mu$m.

In the organic electroluminescence device of the present invention, the light emitting zone means a zone in which a molecule showing luminescence in the solid state is brought into an excited state by directly or indirectly receiving the energy generated by recombination of holes and electrons and emits light.

The molecule showing luminescence in the solid state is not particularly limited, and a light emitting material generally used for organic electroluminescence devices can be used. As the light emitting material, a material having an excellent film-forming property, for example, a luminescent brightening agent, such as a luminescent brightening agent of a condensed polycyclic aromatic compound, a benzoxazole luminescent brightening agent, a benzothiazole luminescent brightening agent, and a benzimidazole luminescent brightening agent; a metal-chelated oxanoid compound; or a distyrylbenzene compound can be used. Examples of the condensed polycyclic aromatic compound include condensed ring light emitting substances having a skeleton of anthracene, naphthalene, phenanthrene, pyrene, chrysene, or perylene.

As the above luminescent brightening agent, such as a benzoxazole luminescent brightening agent, a benzothiazole luminescent brightening agent, and a benzimidazole luminescent brightening agent, the luminescent brightening agents described in the specification of Japanese Patent Application Laid-Open No. Showa 59(1984)-194393 can be used. Representative examples of such luminescent brightening agent include benzoxazole luminescent brightening agents, such as 2,5-bis(5,7-di-t-pentyl-2-benzoxazolyl)-1,3,4-thiadiazole, 4,4'-bis(5,7-t-pentyl-2-benzoxazolyl)stilbene, 4,4'-bis(5,7-di-(2-methyl-2-butyl)-2-benzoxazolyl)stilbene, 2,5-bis(5,7-di-t-pentyl-2-benzoxazolyl)thiophene, 2,5-bis(5-($\alpha,\alpha$-dimethylbenzyl)-2-benzoxazolyl)thiophene, 2,5-bis(5,7-di(2-methyl-2-butyl)-2-benzoxazolyl)-3,4-diphenylthiophene, 2,5-bis(5-methyl-2-benzoxazolyl)thiophene, 4,4'-bis(2-benzoxazolyl)biphenyl, 5-methyl-2-(2-(4-(5-methyl-2-benzoxazolyl)phenyl)vinyl)benzoxazole, and 2-(2-(4-chlorophenyl)vinyl)naphtho(1,2-d)oxazole; benzothiazole luminescent brightening agents, such as 2,2'-(p-phenylenedivinylene)-bisbenzothiazole; and benzimidazole luminescent brightening agents, such as 2-(2-(4-(2-benzimidazolyl)phenyl)vinyl)-benzimidazole and 2-(2-(4-carboxyphenyl)vinyl)benzimidazole. Examples of other compound useful as the light emitting material include the compounds described in "Chemistry of Synthetic Dyes" Pages 628 to 637 and 640 (1971).

As the above metal-chelated oxanoid compound, for example, compounds described in the specification of Japanese Patent Application Laid-Open No. Showa 63(1988)-295695 can be used. Representative examples of such compounds include metal complexes of 8-hydroxyquinoline, such as tris(8-quinolinol)aluminum, bis(8-quinolinol) magnesium, bis(benzo(f)-8-quinolinol)zinc, bis(2-methyl-8-quinolinolato)aluminum oxide, tris(8-quinolinol)indium, tris(5-methyl-8-quinolinol)aluminum, 8-quinolinollithium, tris(5-chloro-8-quinolinol)gallium, bis(5-chloro-8-quinolinol)calcium, and poly(zinc(II)-bis(8-hydroxy-5-quinolinonyl)methane); and dilithium epindridione.

Metal-chelated oxanoid compounds doped with a polycyclic aromatic compound which are described in the specifications of the U.S. Pat. No. 5,141,671 and the U.S. Pat. No. 5,150,006 can also be used. Specific examples of such compounds include metal chelated complexes of 8-hydroxyquinoline, such as bis(2-methyl-8-quinolinolato)(phenolato)aluminum(III), bis(2-methyl-8-quinolinolato)(cresolato)aluminum(III), bis(2-methyl-8-quinolinolato)(phenylphenolato)aluminum(III), bis(2-methyl-8-quinolinolato)(naphtholato)aluminum(III), and bis(2-methyl-8-quinilinolato)aluminum(III)-$\mu$-oxo-bis(2-methyl-8-quinolinolato)aluminum(III), doped with a polycyclic aromatic compound, such as perylene and dibenzoperylene.

As the light emitting compound, other compounds, such as distyrylbenzene derivative described in the specification of European Patent No. 0373582, dimethylidene derivatives described in the specification of European Paten No. 0388768, coumarine derivatives described in the specification of Japanese Patent Application Laid-Open No. Heisei 2(1990)-191694, distyrylpyrazine derivatives described in the specification of Japanese Patent Application Laid-Open No. Heisei 2(1990)-252793, perylene derivatives described in the specification of Japanese Patent Application Laid-Open No. Heisei 2(1990)-196885, naphthalene derivatives described in the specification of Japanese Patent Application Laid-Open No. Heisei 2(1990)-255789, phthaloperynone derivatives described in the specifications of Japanese Patent Application Laid-Open No. Heisei 2(1990)-289676 and Japanese Patent Application Laid-Open No. Heisei 2(1990)-88689, styrylamine derivatives described in the specification of Japanese Patent Application Laid-Open No. Heisei 2(1990)-250292, cyclopentadiene derivatives described in the specification of Japanese Patent Application Laid-Open No. Heisei 2(1990)-289675, and polyphenyl compounds described in the specification of European Patent No. 387715, can be selected and used in accordance with the color of the light which is desired to be emitted and other properties.

The layer of the light emitting zone comprising the above organic compound may have a laminate structure having two or more layers where desired or may be formed by additionally using a fluorescent substance or a polycyclic aromatic compound in such a manner as that described in the specifications of the U.S. Pat. No. 4,769,292 and the U.S. Pat. No. 5,141,671. In this case, the above organic compound has a form of a layer of a thin film and exhibits the function of injection and a part of the function of light emission which are the functions of the light emitting zone. The fluorescent substance is present in the thin film of the organic compound in a small amount (several percent by mol or less) and exhibits a part of the function of light emission by emitting light in response with the recombination of electrons and holes.

The layer of the light emitting zone may be constituted with a single layer comprising one or more types of the light emitting material or a laminate of layers of different light emitting materials.

In the organic luminescence device of the present invention, other layers may be formed between the anode and the cathode in addition to the layer of the hole transporting zone and the layer of the light emitting zone which are described above, where necessary, for example, to increase the efficiency of injection of electrons from the cathode or to improve the adhesion of a layer to the anode.

In the following, preferable examples of preparation of the organic electroluminescent device of the present invention are described. At fist, a thin film comprising a desired electrode material, such as a material for the anode, is formed on a suitable substrate to a thickness of 500 nm or less, preferably in the range of 10 to 20 nm, by a method, such as the vapor deposition and the sputtering, to prepare an anode. On the prepared anode, thin films comprising materials constituting the device, i. e., materials for the hole injecting layer, the hole transporting layer, and the layer of light emitting zone, are formed.

As the method of forming the thin films, the spin-coating, the casting, or the vapor deposition can be used. The vacuum vapor deposition is preferable because a uniform film is easily obtained, and the formation of pin-holes can be prevented more easily. The condition of the vacuum vapor deposition is different depending on the type of the used compound as well as the crystal structure and the association structure which are desired to be formed in the molecular deposition film. In general, it is preferred that the conditions are selected in the following range: a temperature of a heated boat of 50 to 400° C., a vacuum of $10^{-6}$ to $10^{-3}$ Pa, a rate of vapor deposition of 0.01 to 50 nm/sec, a substrate temperature of –50 to 300° C., and a film thickness of 5 nm to 5 $\mu$m.

After these layers have been formed, a thin film comprising a cathode material is formed on the formed layers by a method, such as the vapor deposition or the sputtering, to a thickness of 500 nm or less, preferably in the range of 10 to 200 nm, to form a cathode. Thus, the desired electroluminescence device can be prepared. For the preparation of the electroluminescence device, the procedures for the preparation may be conducted in the reversed order.

The electroluminescence device of the present invention which can be prepared as described above emits light by applying a direct voltage of 3 to 40 V in the condition that the anode is connected to a positive electrode (+) and the cathode is connected to a negative electrode (–). When the connection is reversed, no electric current is observed and no light is emitted at all. When an alternating voltage is applied to the electroluminescence device, light emission is observed only in the condition that the polarity of the anode is positive and the polarity of the cathode is negative. When an alternating voltage is applied to the organic EL device, any type of wave shape can be used.

It is preferred that the device of the present invention is supported on a support. The support is not particularly limited, and a support conventionally used in organic electroluminescence devices, such as glass, a transparent plastic, and quartz, can be used.

The present invention also provides an organic thin film comprising two layers which are a layer containing a compound represented by general formula (I) and having a thickness of 5 nm to 5 $\mu$m and a layer containing a compound represented by general formula (II) and having a thickness of 5 nm to 5 $\mu$m. This organic thin film has very excellent hole injecting and transporting properties and can advantageously be used for organic electroluminescence devices. This organic thin film can also be used widely for other organic devices and photosensitive films in the electronic photography.

This organic thin film can be prepared by the same process as that used for preparation of the hole injection layer and the hole transporting layer in the preparation of the above organic electroluminescence device.

In the following, the novel triamine compound which is another object of the present invention is described. The triamine compound of the present invention is a compound having a structure represented by general formula (III):

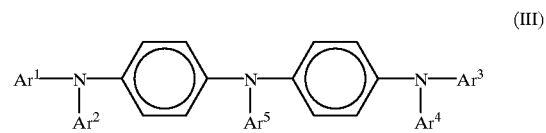

(III)

[wherein $Ar^1$ to $Ar^4$ represent each an aryl group having 6 to 18 core carbon atoms which is unsubstituted or substituted with an alkyl group, an alkoxy group, vinyl group, or styryl group and may be the same with each other or different from each other, and $Ar^5$ represents biphenyl group which is unsubstituted or substituted].

In above general formula (III), $Ar^5$ preferably represents an aryl group represented by:

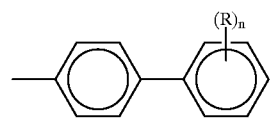

[wherein R represents hydrogen, an alkyl group having 1 to 6 carbon atoms, an alkoxy group having 1 to 6 carbon atoms, or phenyl group; n represents an integer of 0 to 5; and when a plurality of R are present, the plurality of R may be the same with each other or different from each other], and $Ar^1$ to $Ar^4$ represent each an aryl group represented by any of the general formulae:

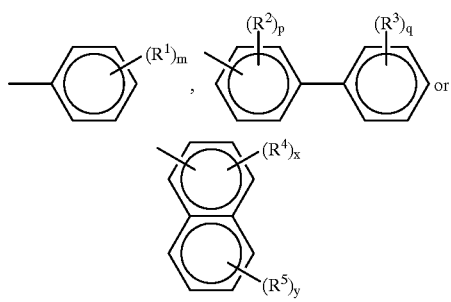

$R^1$ to $R^5$ in the above formulae represent each hydrogen, an alkyl group having 1 to 6 carbon atoms, an alkoxy group having 1 to 6 carbon atoms, or phenyl group. m represents an integer of 0 to 5, p represents an integer of 0 to 4, q represents an integer of 0 to 5, x represents an integer of 0 to 3, and y represents an integer of 0 to 4. When a plurality of $R^1$, $R^2$, $R^3$, $R^4$, or $R^5$ are present, the plurality of $R^1$, $R^2$, $R^3$, $R^4$, or $R^5$ be the same with each other or different from each other. $Ar^1$ to $Ar^4$ may be the same with each other or different from each other. R represents hydrogen, an alkyl group having 1 to 6 carbon atoms, an alkoxy group having 1 to 6 carbon atoms, or phenyl group; n represents an integer of 0 to 5; and when a plurality of R are present, the plurality of R may be the same with each other or different from each other.

The alkyl group having 1 to 6 carbon atoms which is represented by any of $R^1$ to $R^5$ and R may be linear, branched, or cyclic. Specific examples of the alkyl group having 1 to 6 carbon atoms include methyl group, ethyl group, n-propyl group, isopropyl group, n-butyl group, isobutyl group, sec-butyl group, tert-butyl group, n-pentyl group, isopentyl group, n-hexyl group, isohexyl group, cyclopropyl group, cyclobutyl group, cyclopentyl group, and cyclohexyl group. The alkoxy group having 1 to 6 carbon atoms which is represented by any of $R^1$ to $R^5$ and R may be linear, branched, or cyclic. Specific examples of the alkoxy group having 1 to 6 carbon atoms include methoxy group, ethoxy group, n-propoxy group, isopropoxy group, n-butoxy group, isobutoxy group, sec-butoxy group, tert-butoxy group, n-pentoxy group, isopentoxy group, n-hexoxy group, isohexoxy group, cyclopropoxy group, cyclobutoxy group, cyclopentoxy group, and cyclohexoxy group.

Examples of the above triamine compound represented by general formula (III) include the following compounds:

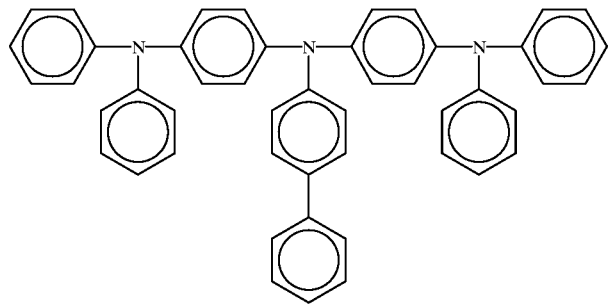

(1)

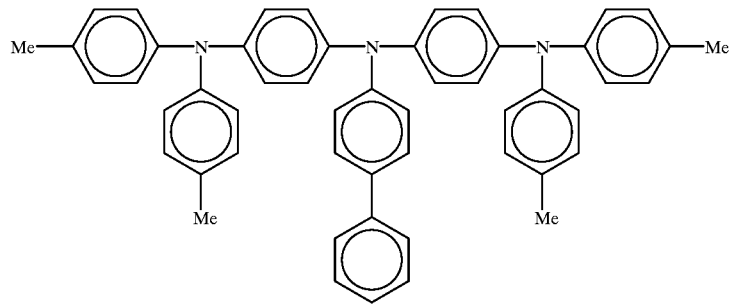

(2)

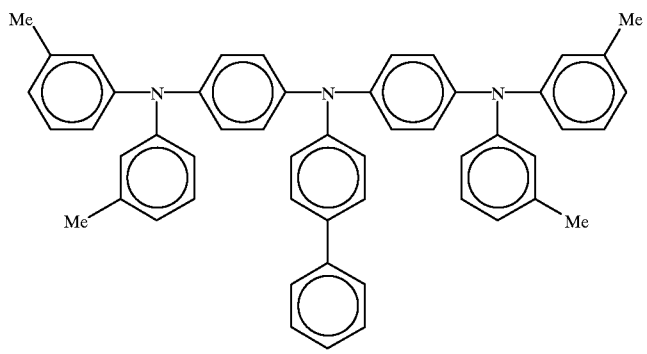
(3)
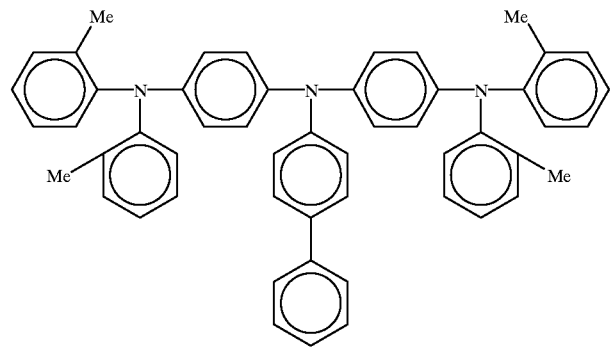
(4)
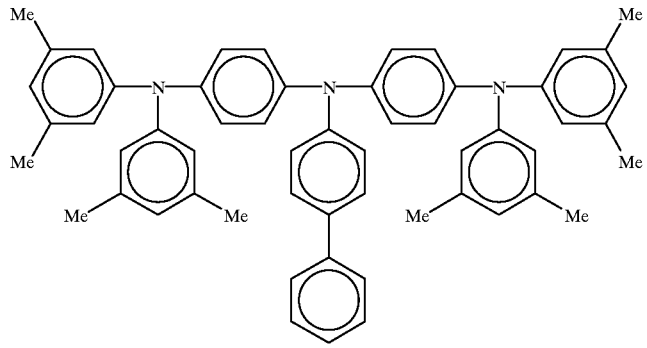
(5)
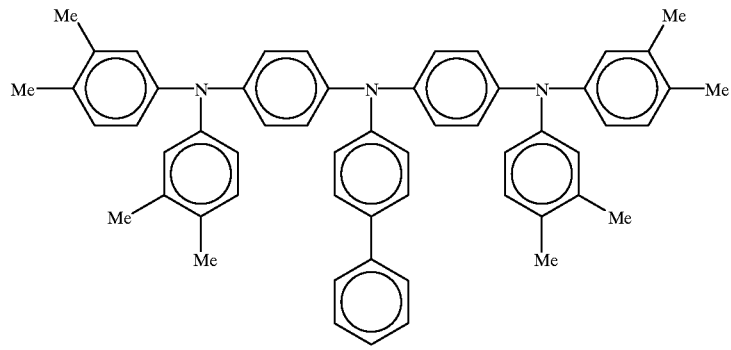
(6)

-continued
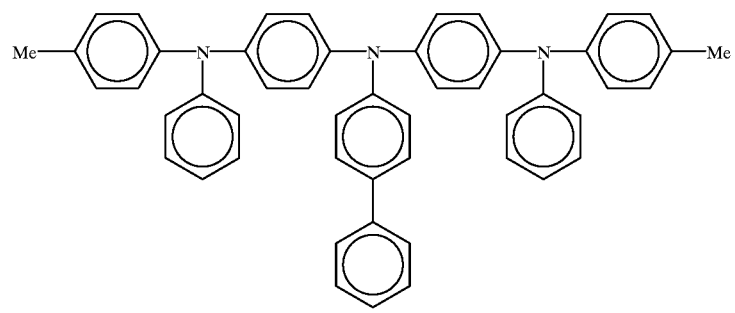
(7)
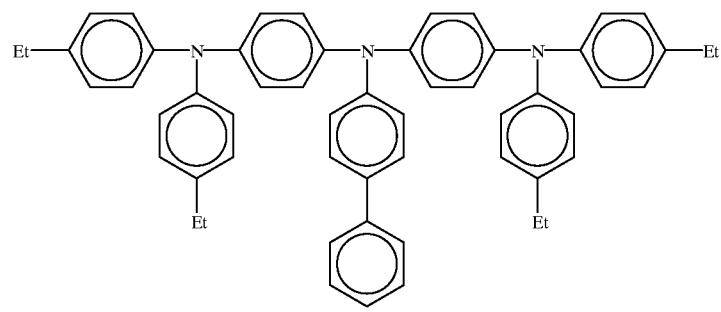
(8)
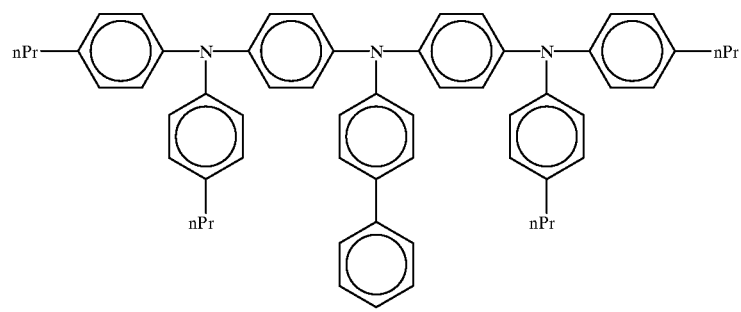
(9)
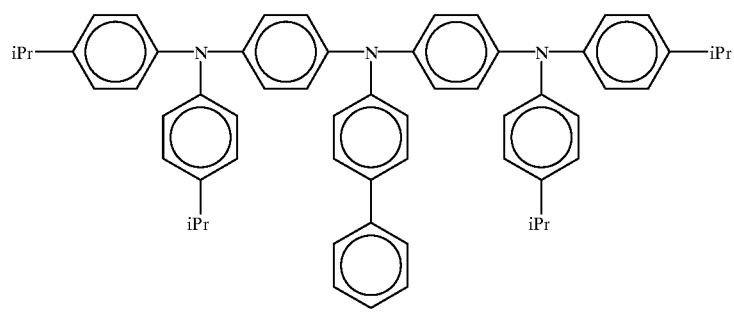
(10)
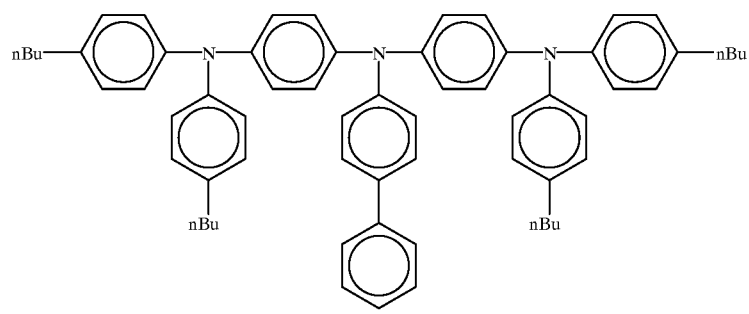
(11)

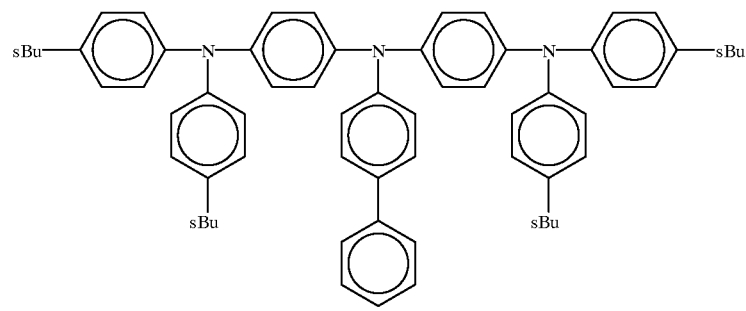
(12)
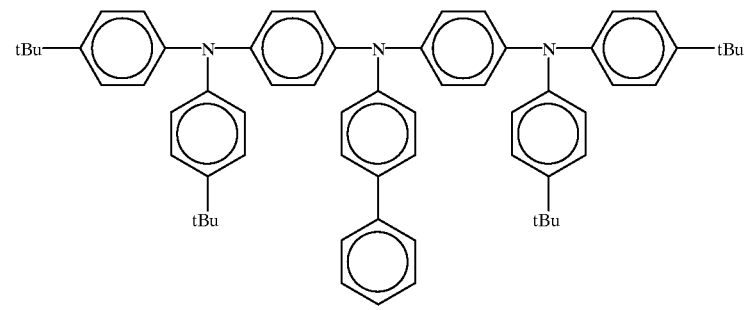
(13)
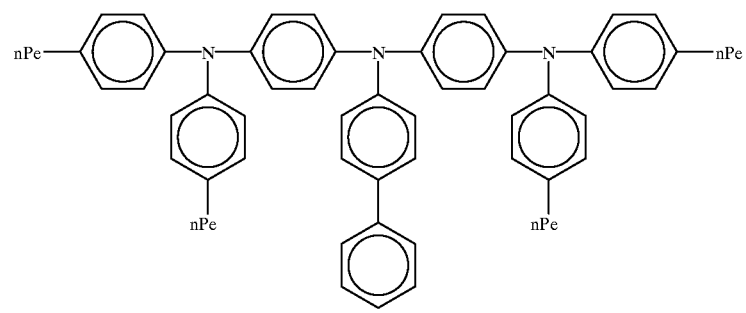
(14)
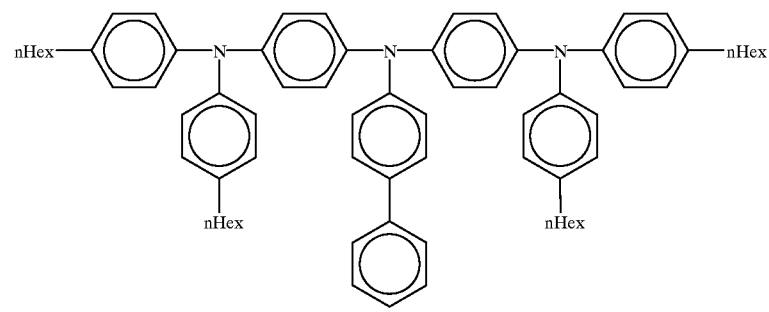
(15)
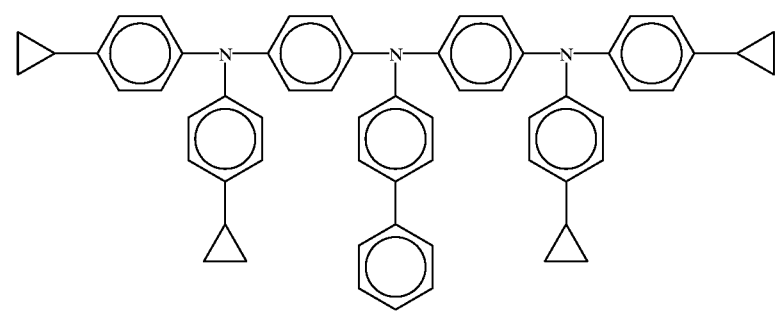
(16)

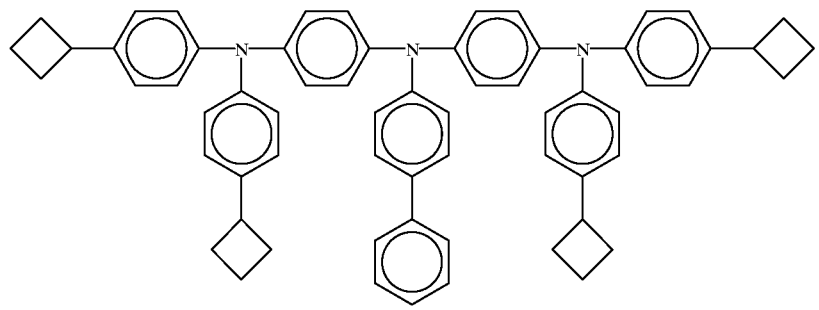
(17)
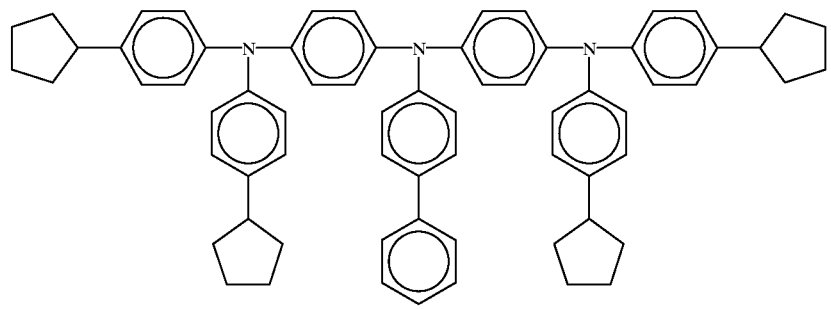
(18)
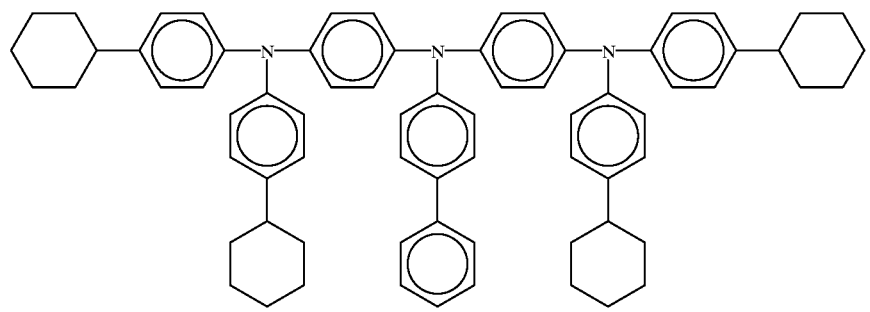
(19)
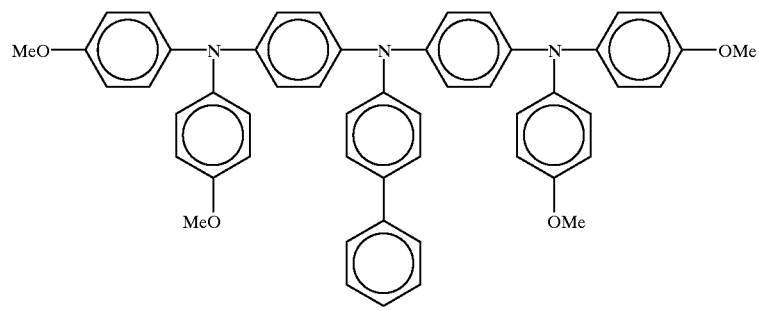
(20)

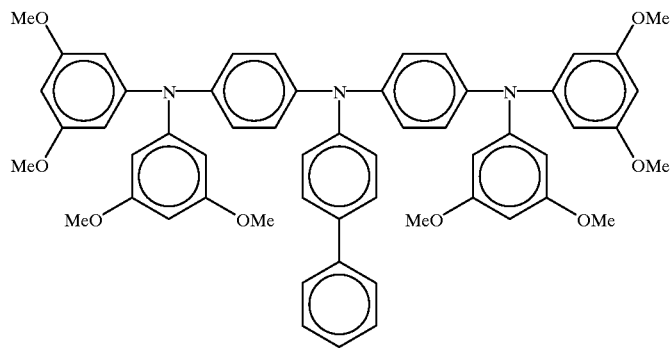
(21)
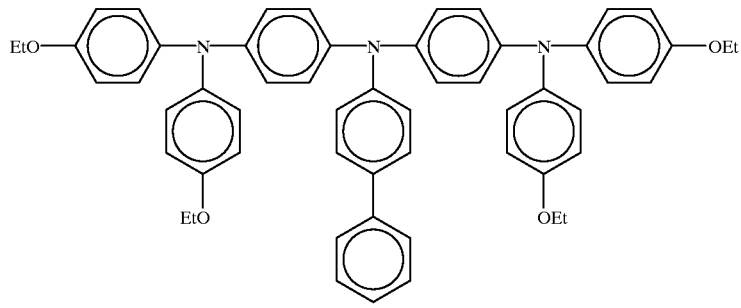
(22)
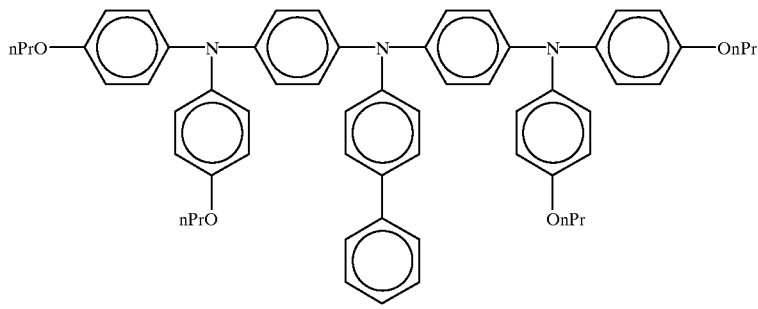
(23)
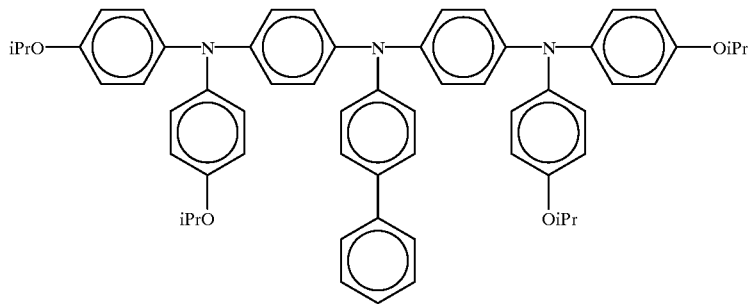
(24)

-continued
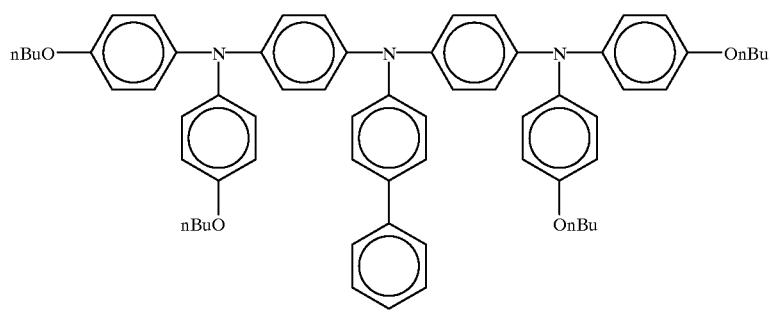
(25)
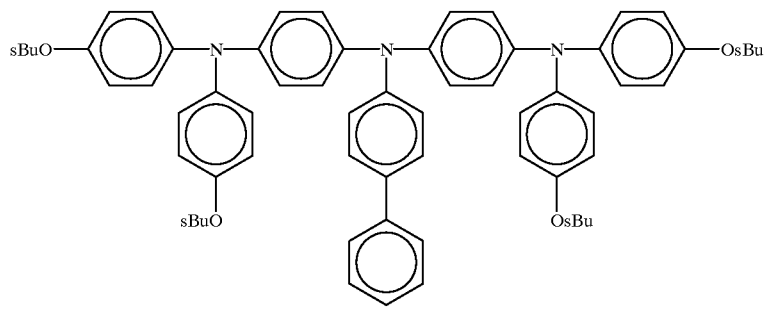
(26)
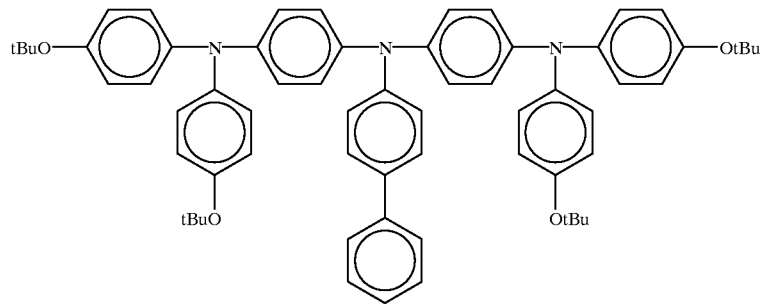
(27)
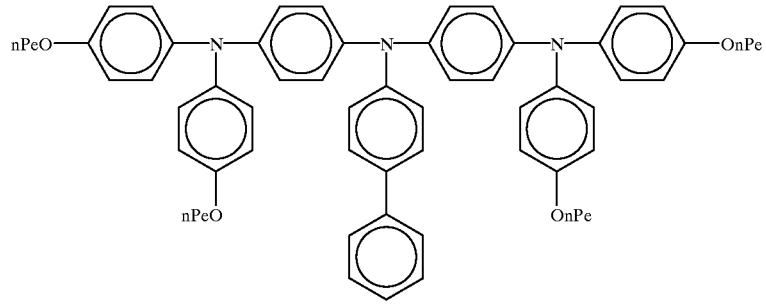
(28)
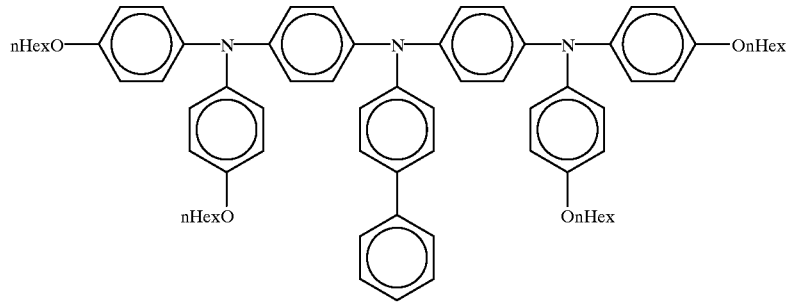
(29)

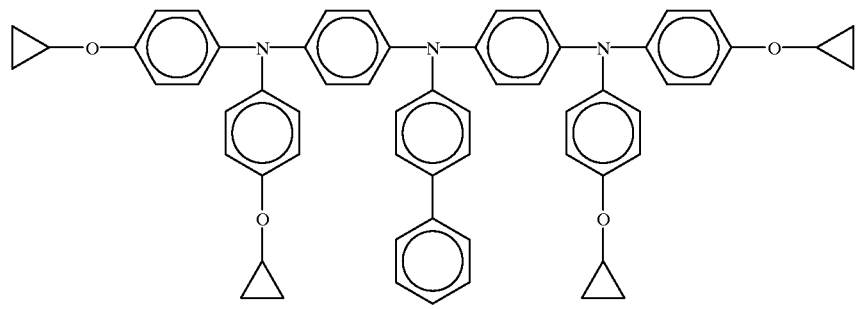
(30)
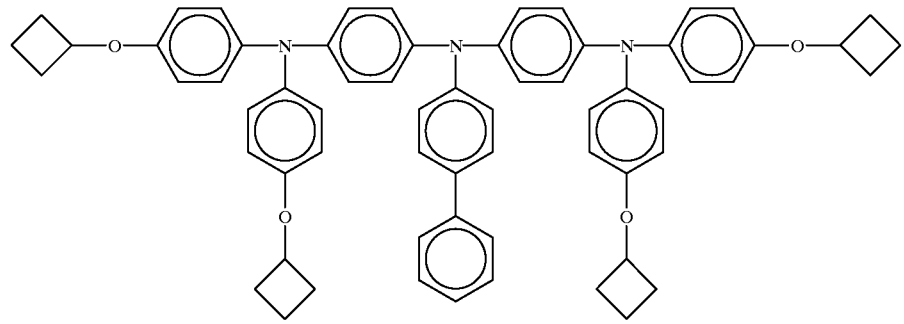
(31)
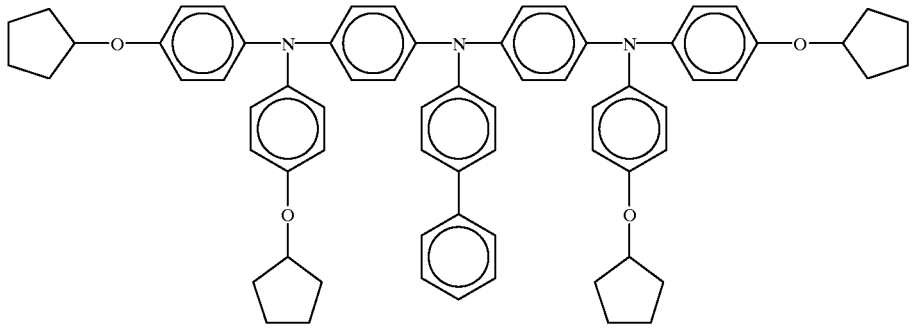
(32)
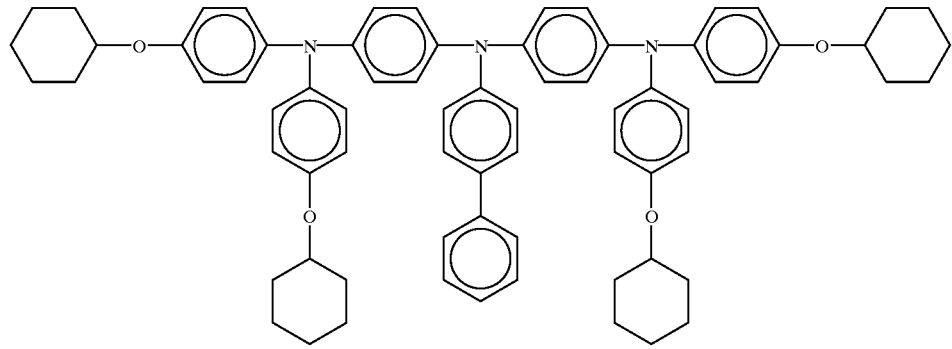
(33)

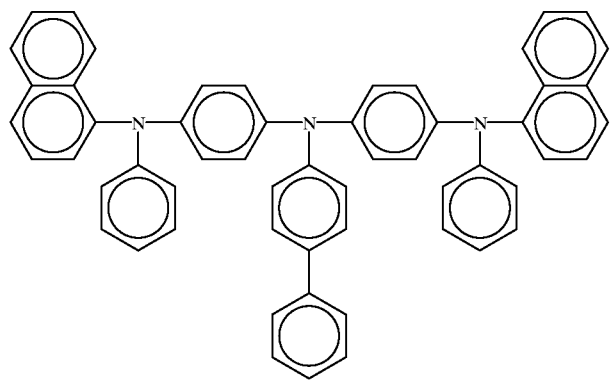
(34)
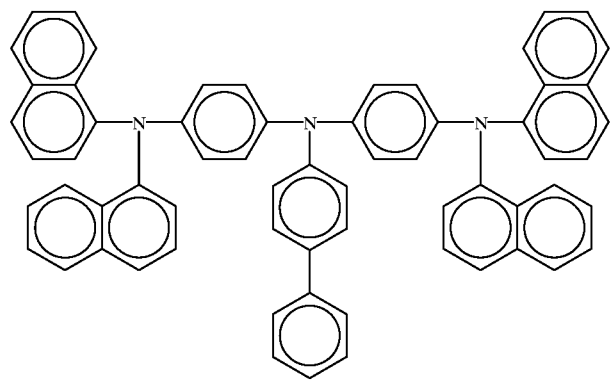
(35)
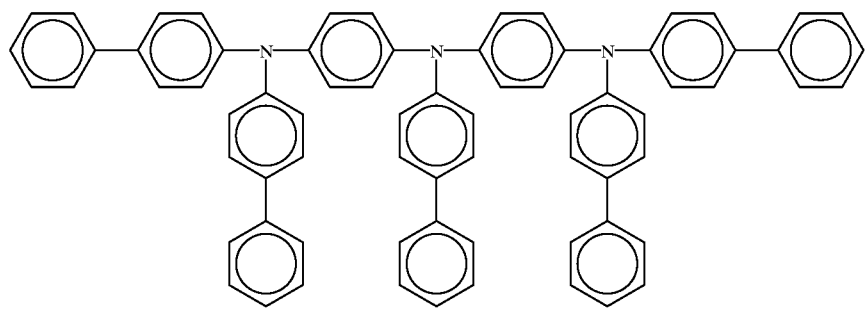
(36)
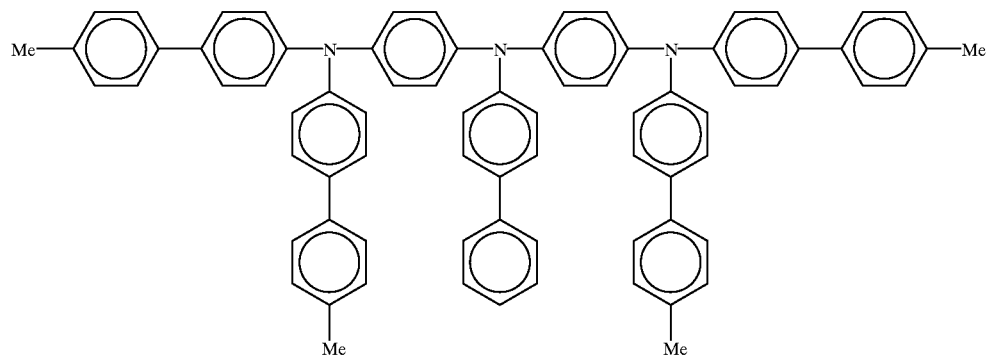
(37)

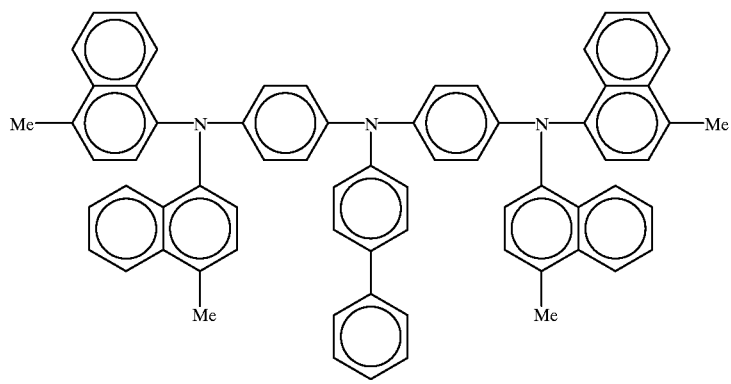
(38)
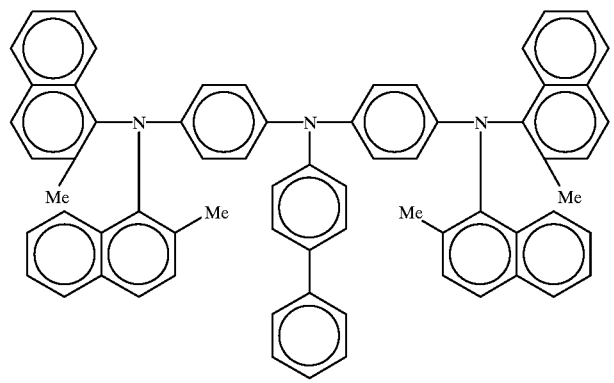
(39)
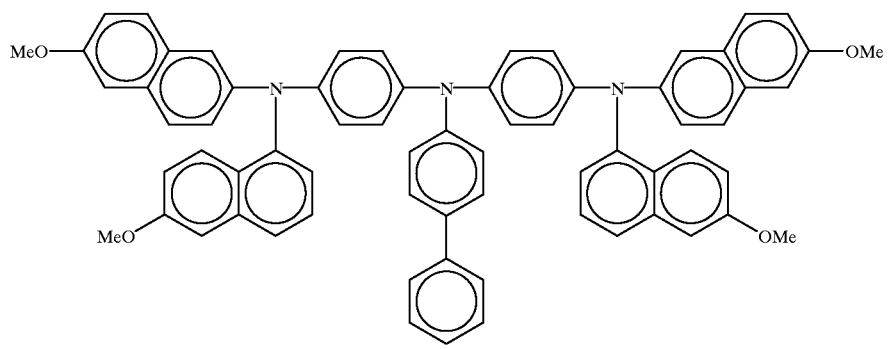
(40)
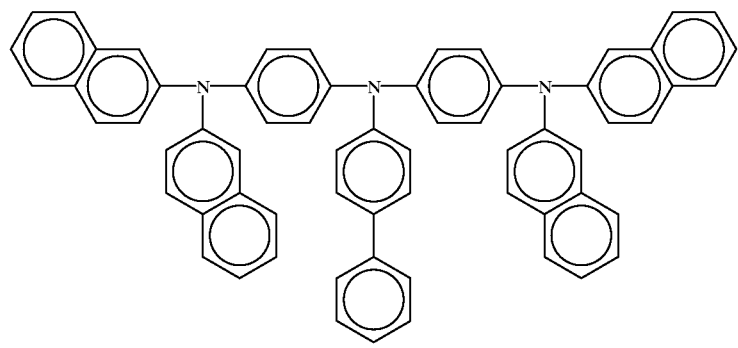
(41)

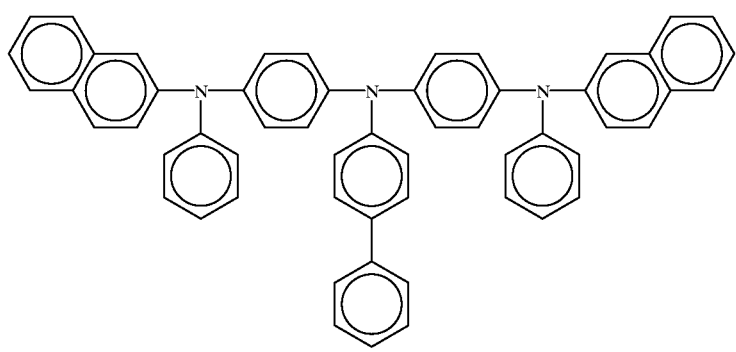
(42)
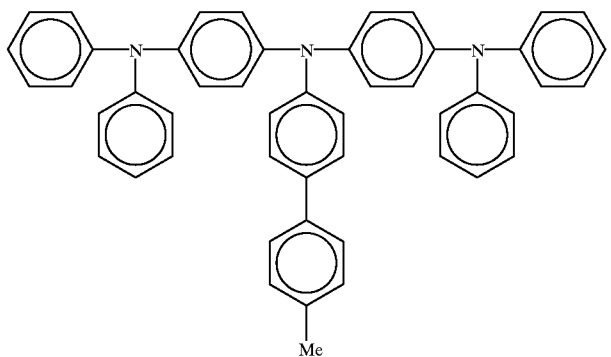
(43)
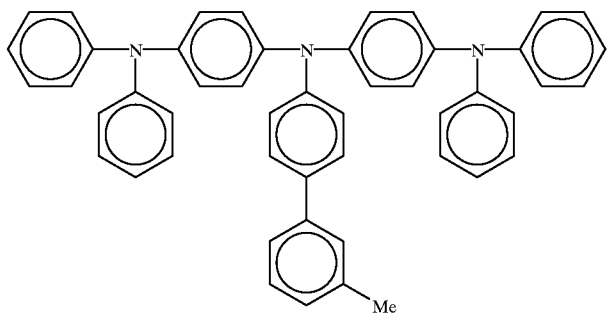
(44)
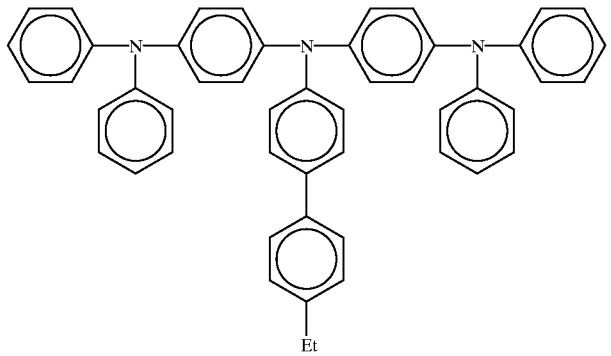
(45)

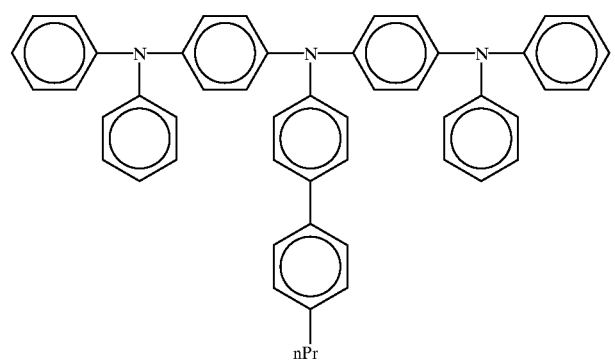
(46)
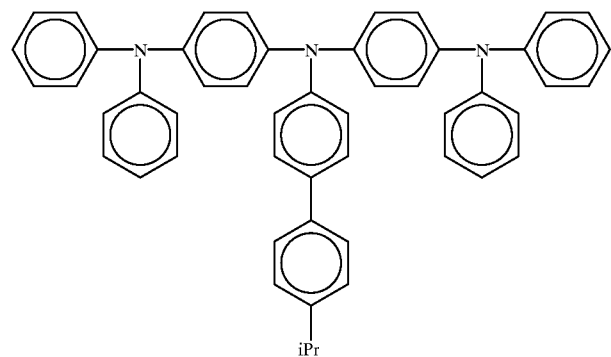
(47)
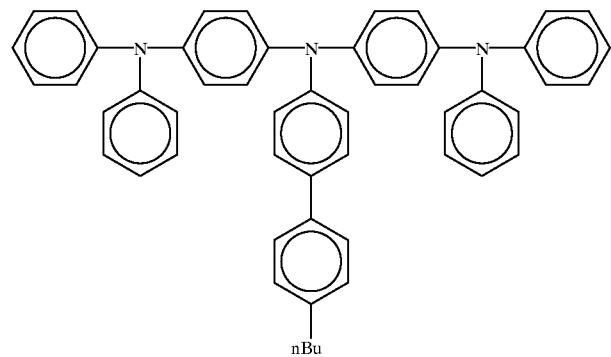
(48)
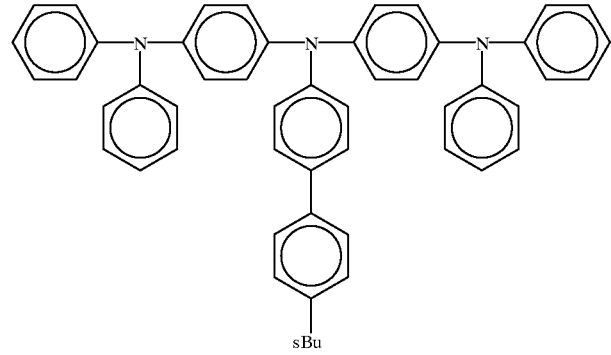
(49)

(50)
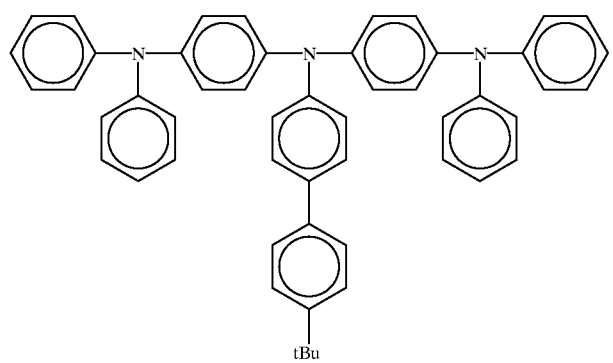
(51)
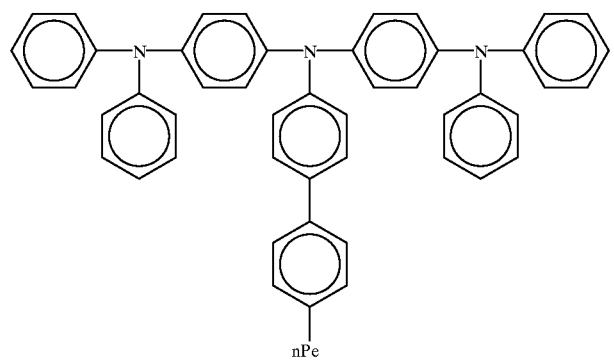
(52)
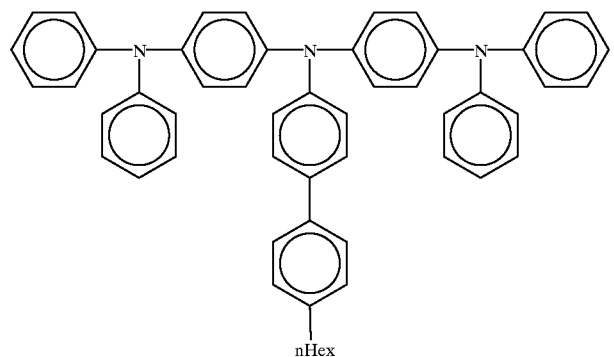
(53)
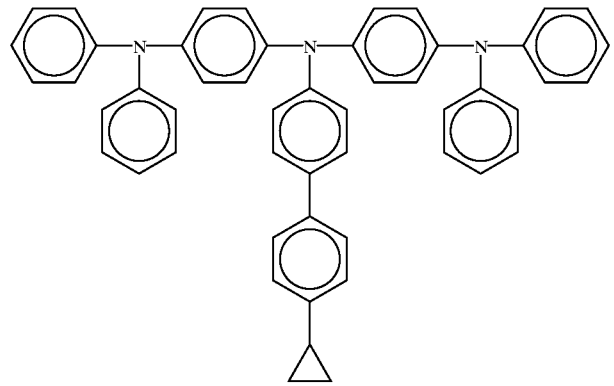

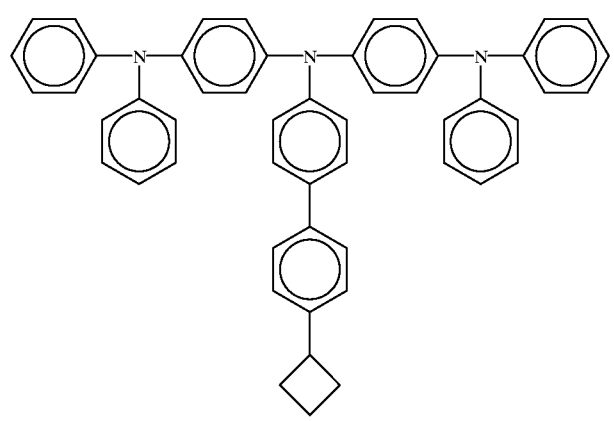
(54)
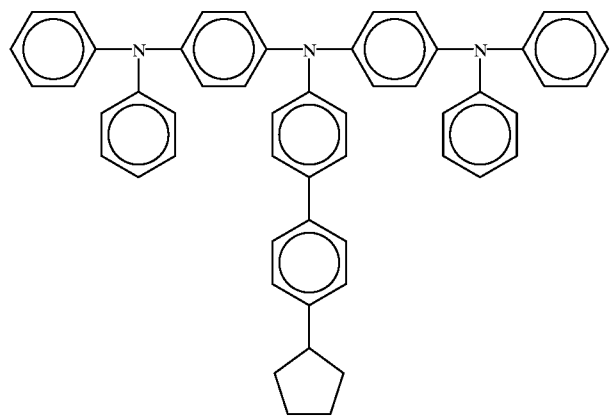
(55)
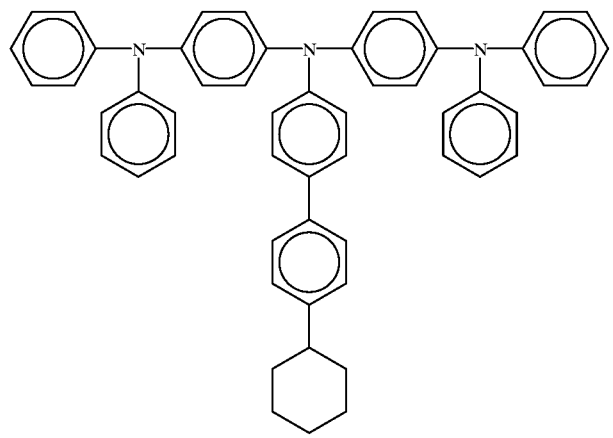
(56)

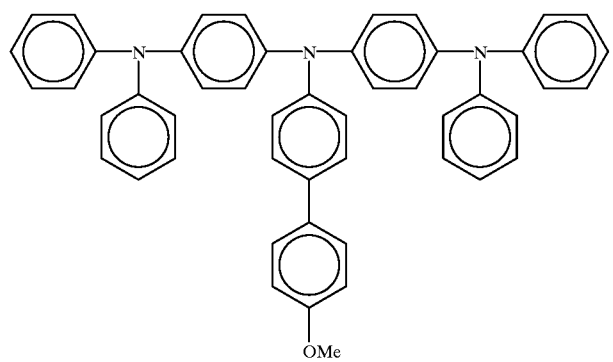
(57)
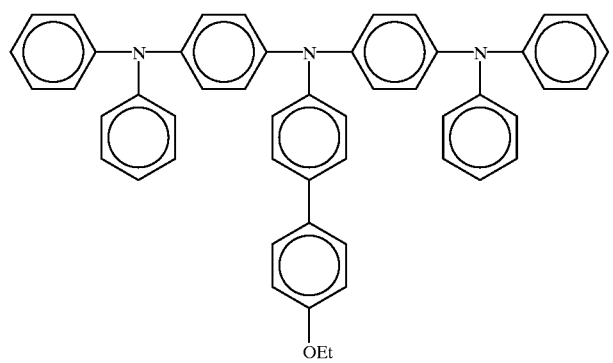
(58)
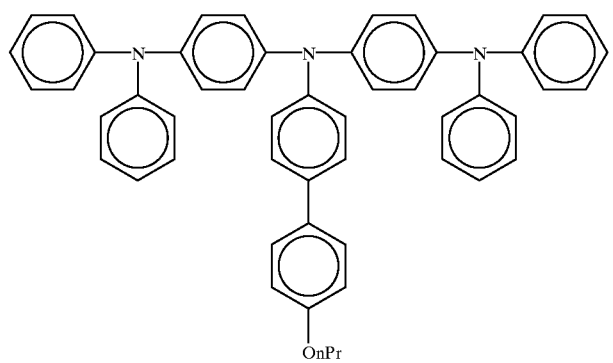
(59)
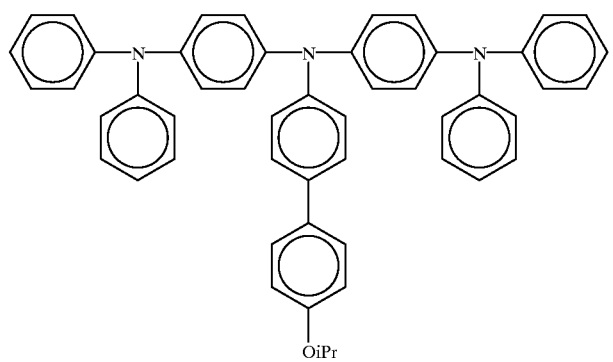
(60)

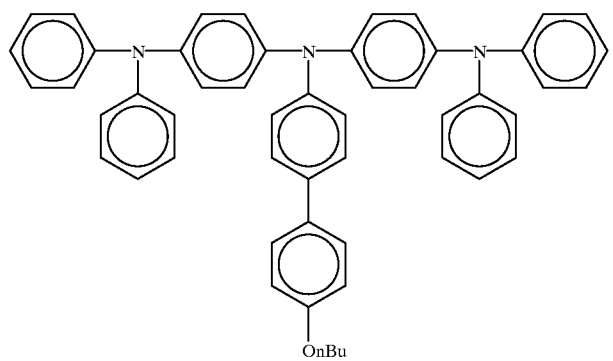
(61)
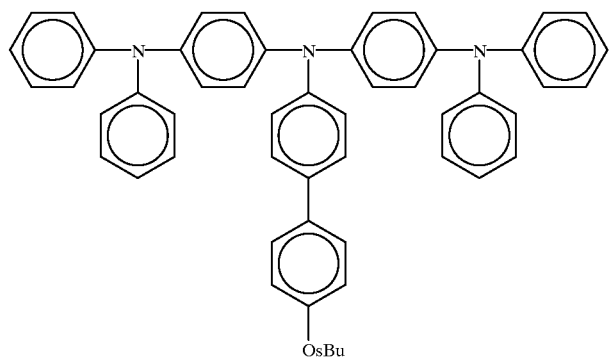
(62)
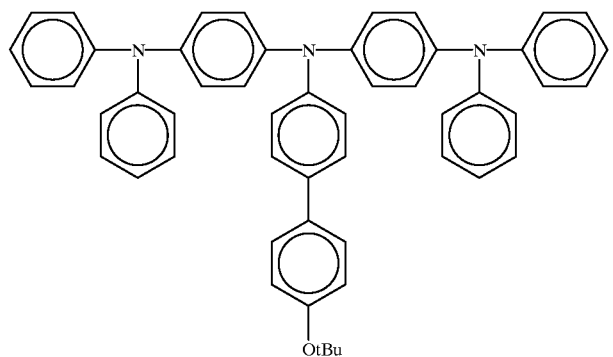
(63)
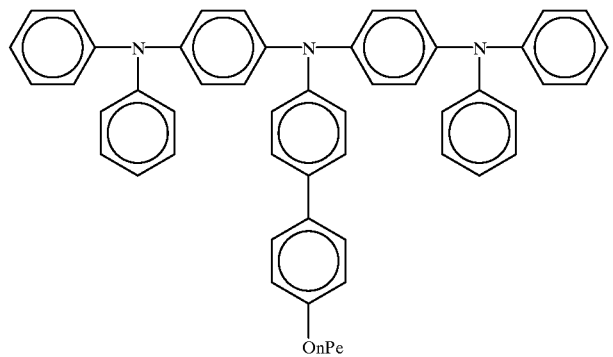
(64)

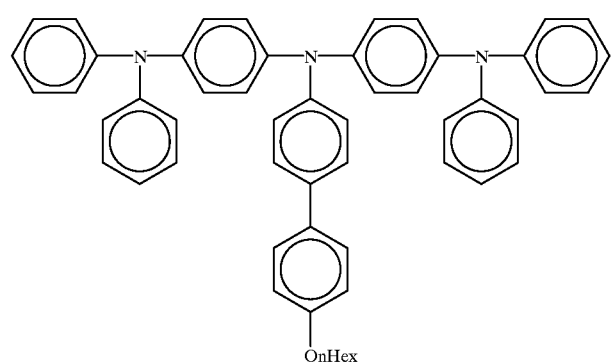
(65)
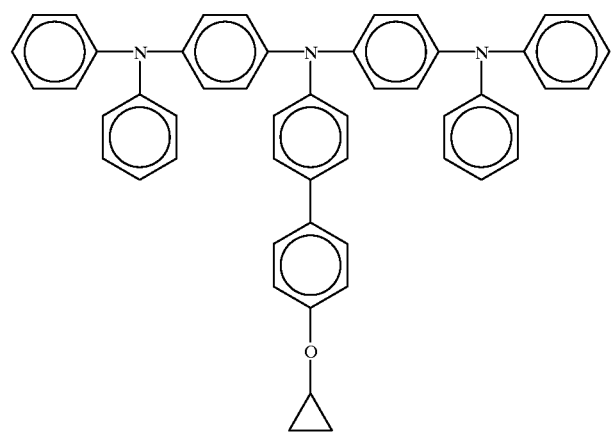
(66)
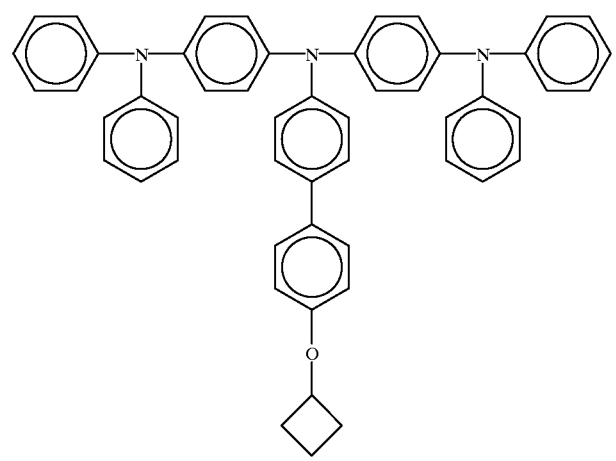
(67)

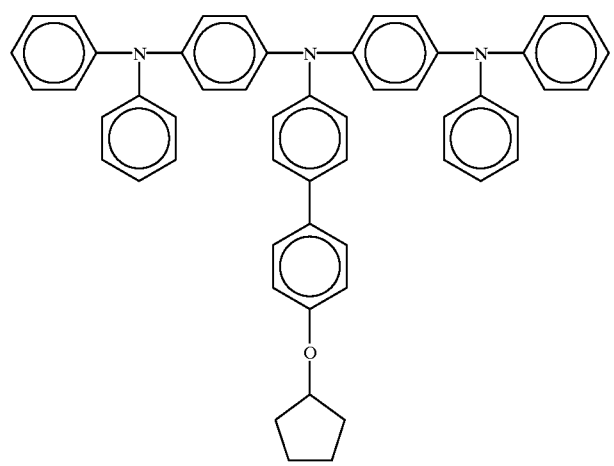
(68)
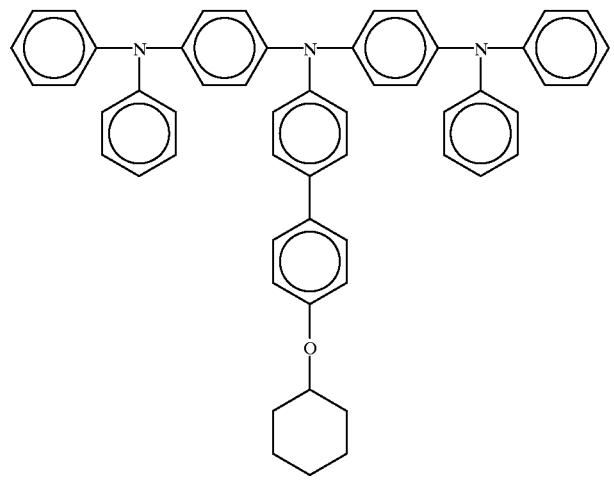
(69)
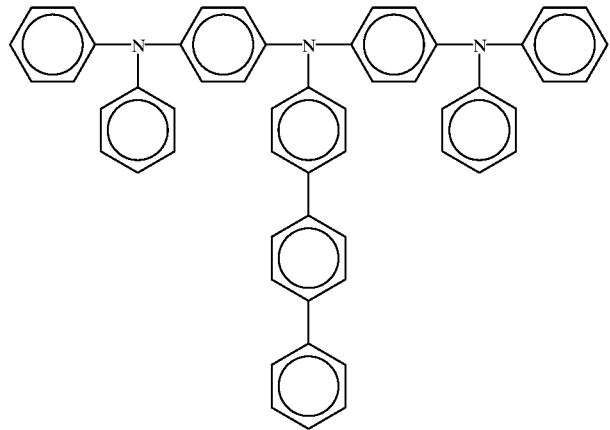
(70)

-continued

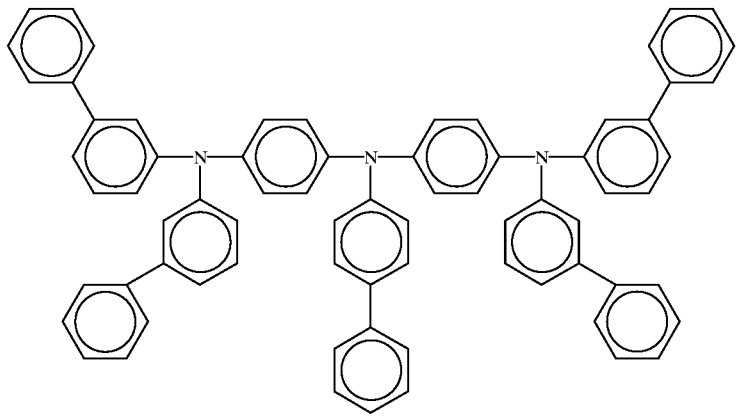

(71)

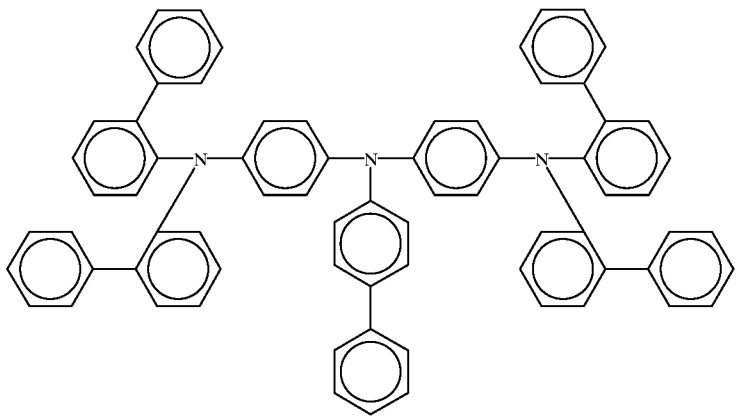

(72)

In the above formulae, the abbreviations represent groups as follows: Me: methyl group, Et: ethyl group, nPr: n-propyl group, iPr: isopropyl group, nBu: n-butyl group, sBu: sec-butyl group, tBu: tert-butyl group, nPe: n-pentyl group, and nHex: n-hexyl group.

The present invention is described in more detail with reference to examples. However, the present invention is not limited by the examples.

EXAMPLE 1

Preparation of HI-3

(1) Into a 500 ml three-necked flask, 16.5 g of aniline (a product of HIROSHIMA WAKO Co., Ltd.), 50 g of p-fluoronitrobenzene (a product of HIROSHIMA WAKO Co., Ltd.), 1 g of copper powder, 48.9 g anhydrous potassium carbonate, and 330 ml of DMF (dimethylformamide) were placed, and the reaction was allowed to proceed in the resultant mixture at 150° C. for 8 hours.

After the reaction had been completed, the reaction mixture was cooled, and salts were removed from the reaction mixture by filtration. The obtained filtrate was poured into 3 liters of water, and the formed crystal in an amount of 40 g was separated by filtration. The separated crystal was dissolved into 600 ml of DMF. To the resultant solution, 8 g of a 5% Pd—C was added, and the hydrogenation was conducted under an atmospheric pressure for 4 hours by bubbling hydrogen gas through the reaction mixture.

After the reaction had been completed, the Pd—C was removed from the reaction mixture by filtration. The obtained filtrate was poured into 4 liters of water, and the precipitated crystal was separated by filtration to obtain 28 g of 4,4'-diamino-triphenylamine.

(2) Into a 300 ml three-necked flask, 1.0 g of 4,4'-diamino-triphenylamine obtained above in (1), 4.0 g of 3-iodotoluene (a product of TOKYO KASEI Co., Ltd.), 3 g of anhydrous potassium carbonate, and 1 g of copper powder (a product of HIROSHIMA WAKO Co., Ltd.) were placed and then dissolved in 200 ml of dimethylsulfoxide (DMSO). The reaction was allowed to proceed in the obtained mixture at 200° C. for 8 hours while the mixture was stirred.

After the reaction had been completed, the reaction mixture was filtered, and the obtained filtrate was extracted with methylene chloride. From the obtained extract, the solvent was removed by using a rotary evaporator, and the residual product was purified by using a column packed with silica-gel (a product of HIROSHIMA WAKO Co., Ltd.) with toluene as the developing solvent to obtain 0.78 g of a light yellow powder.

This product was identified as 4,4'-bis[N,N-di(3-tolyl)amino]-triphenylamine (HI-3) by the measurements of NMR and FD-MS (field diffusion mass spectrum).

EXAMPLE 2

Preparation of HI-16

The reactions and the purifications were conducted in accordance with the same procedures as those conducted in Example 1 except that 4.0 g of 4-iodoanisol (a product of HIROSHIMA WAKO Co., Ltd.) was used in place of 3-iodotoluene used in Example 1 (2), and 0.66 g of a light yellow powder was obtained.

This product was identified as 4,4'-bis[N,N-di(4-methoxyphenyl)amino]triphenylamine (HI-16) by the measurements of NMR and FD-MS.

EXAMPLE 3

Preparation of HI-35

(1) Into a 500 ml three-necked flask, 75 g of biphenyl (a product of HIROSHIMA WAKO Co., Ltd.), 19.2 g of ortho-periodic acid (a product of HIROSHIMA WAKO Co., Ltd.), 64.3 g of iodine, 230 ml of acetic acid, and 7.6 ml of concentrated sulfuric acid were placed, and the reaction was allowed to proceed in the resultant mixture at 70° C. for 2 hours.

After the reaction had been finished, the reaction mixture was cooled and then poured into 1 liter of methanol while methanol was stirred. The precipitated crystal was separated by filtration and then recrystallized by using 2 liters of acetonitrile to obtain 7.2 g of 4-iodobiphenyl.

(2) Then, the reactions and the purifications were conducted in accordance with the same procedures as those conducted in Example 1 except that 5.0 g of 4-iodobiphenyl obtained above in (1) was used in place of 3-iodotoluene used in Example 1 (2), and 0.34 g of a light yellow powder was obtained.

This product was identified as 4,4''-bis[N,N-di(dipheno-4-yl)amino]triphenylamine (HI-35) by the measurements of NMR and FD-MS.

Preparation Example 1

Preparation of HT-23

The reactions and the purifications were conducted in accordance with the same procedures as those conducted in Example 1 except that 2.0 g of N,N'-diphenyl-4,4'-benzidine was used in place of 4,4'-diamino-triphenylamine used in Example 1 (2), and 1.6 g of a white powder was obtained.

This product was identified as N,N'-bis(3-tolyl)-N,N'-diphenyl-4,4'-benzidine (HT-23) by the measurements of NMR and FD-MS.

Preparation Example 2

Preparation of HT-39

(1) A mixture of 20 g of 4-iodobiphenyl obtained above in Example 3 (1) and 150 ml of acetic acid was heated to 80° C., and 40 ml of fuming nitric acid was added dropwise to the heated mixture at 75 to 90° C. during 2 hours. After the resultant mixture was kept being stirred for 1 hour at this temperature, the mixture was cooled to 50° C., and 200 ml of methanol was added to the cooled mixture to obtain 11 g of a light yellow crystal after filtration.

The obtained product was heated with a mixture of 1.6 g of aniline (a product of HIROSHIMA WAKO Co., Ltd.), 100 ml of nitrobenzene, 1 g of copper powder, and 10 g of anhydrous potassium carbonate at 200° C., and the reaction was allowed to proceed for 48 hours. The insoluble portion was then removed from the reaction product by filtration. After the solvent was removed from the filtrate by the vacuum distillation, the residual product was recrystallized by using 200 ml of ethanol to obtain 8 g of a crystal.

The obtained crystal was dissolved in 200 ml of DMF. To the resultant solution, 2 g of a 5% Pd—C was added, and the hydrogenation was conducted under an atmospheric pressure for 4 hours by bubbling hydrogen gas through the reaction mixture.

The insoluble portion was removed from the reaction product by filtration, and the obtained filtrate was poured into 1 liter of water saturated with sodium chloride. The precipitated crystal was separated by filtration and reprecipitated by using 500 ml of toluene to obtain 5 g of 4,4'-bis(4-aminophenyl)triphenylamine.

(2) The reactions and the purifications were conducted in accordance with the same procedures as those conducted in Example 1 (2) except that 1.0 g of 4,4'-bis(4-aminophenyl)triphenylamine obtained above in (1) was used in place of 4,4'-diamino-triphenylamine used in Example 1 (2), and 3.0 g of iodobenzene (a product of HIROSHIMA WAKO Co., Ltd.) was used in place of 3-iodotoluene used in Example 1 (2), and 0.31 g of a white powder was obtained.

This product was identified as 4,4'-bis[4-(N,N-diphenylamino)phenyl]triphenylamine (HT-39) by the measurements of NMR and FD-MS.

Preparation Example 3

Preparation of DPVBi (1) To 150 ml of carbon tetrachloride, 10 g of 4,4'-dimethylbiphenyl (a product of ALDRICH Co.), 20 g of N-bromosuccinimide (a product of HIROSHIMA WAKO Co., Ltd.), and 0.9 g of benzoyl peroxide (a product of HIROSHIMA WAKO Co., Ltd.) were added, and the reaction was allowed to proceed in the resultant mixture at 90° C. for 2 hours while the mixture was stirred.

After the reaction product was cooled, the precipitated crystal was washed with 100 ml of methanol to obtain 13.2 g of 4,4'-dibromomethyl-biphenyl.

(2) Into a 300 ml three-necked flask, 1.0 g of 4,4'-dibromomethyl-biphenyl obtained above in (1), 3.0 g of benzophenone (a product of TOKYO KASEI Co., Ltd.), and 0.50 g of potassium t-butoxide (a product of HIROSHIMA WAKO Co., Ltd.) were placed and then dissolved in 150 ml of DMSO. The reaction was allowed to proceed in the resultant solution at a room temperature for 2 hours while the solution was stirred.

After the reaction had been completed, the reaction solution was extracted with toluene, and then the solvent was removed from the extract by distillation using a rotary evaporator. The residual product was purified by using a column packed with silica-gel (a product of HIROSHIMA WAKO Co., Ltd.) with toluene as the developing solvent to obtain 1.1 g of a white powder.

This product was identified as 4,4'-bis(2,2-diphenyl-1-vinyl)-1,1'-biphenyl (DPVBi) by the measurements of NMR and FD-MS.

Preparation Example 4

Preparation of MTDATA

The reactions and the purifications were conducted in accordance with the same procedures as those conducted in Example 1 (2) except that 1.0 g of 4,4',4''-triiodotriphenylamine was used in place of 3-iodotoluene used in Example 1 (2), and 1.0 g of N-(3-tolyl)-N-phenylamine (a product of ALDRICH Co.) was used in place of 4,4'-diaminotriphenylamine used in Example 1 (2), and 0.30 g of a light yellow powder was obtained.

This product was identified as 4,4',4"-tris[N-(3-tolyl)-N-phenylamino]triphenylamine (MTDATA) by the measurements of NMR and FD-MS.

Preparation Example 5
Preparation of TA-1

Into a 300 ml three-necked flask, 2.0 g of N,N'-diphenyl-1,4-phenylenediamine (a product of KANTO KAGAKU Co., Ltd.), 50 ml of 4-fluoronitrobenzene (a product of HIROSHIMA WAKO Co., Ltd.), 5 g of anhydrous potassium carbonate, and 1 g of copper powder were placed, and the reaction was allowed to proceed in the resultant mixture at 200° C. for 8 hours while the mixture was stirred.

After the reaction had been completed, the reaction mixture was filtered. The obtained filtrate was extracted with methylene chloride, and the solvent was removed from the obtained extract by distillation. The residual product was purified by using a column packed with silica-gel (a product of HIROSHIMA WAKO Co., Ltd.) with toluene as the developing solvent.

The obtained product was dissolved in 100 ml of dimethylformamide (DMF). To the resultant solution, 10 g of a 5% by weight Pd—C was added, and the reaction was allowed to proceed in the resultant mixture for 8 hours under a hydrogen stream. The reaction mixture was filtered, and the solvent was removed from the obtained filtrate. The residual product was dissolved in 100 ml of iodobenzene (a product of HIROSHIMA WAKO Co., Ltd.). To the obtained solution, 10 g of anhydrous potassium carbonate and 1 g of copper powder were added, and the reaction was allowed to proceed in the resultant mixture at 200° C. for 8 hours.

After the reaction had been completed, the reaction mixture was filtered. The obtained filtrate was extracted with methylene chloride, and the solvent was removed from the obtained extract by using a rotary evaporator. The residual product was purified by using a column packed with silica-gel with toluene as the developing solvent to obtain 0.24 g of a yellow powder.

This product was identified as N,N'-bis[4-(N,N-diphenylamino)phenyl]-N,N'-diphenyl-1,4-phenylenediamine (TA-1) by the measurements of NMR and FD-MS.

EXAMPLE 4

On a glass substrate having the size of 25 mm×75 mm×1.1 mm, an ITO electrode was formed to the thickness of 100 nm, and the obtained product was used as the transparent substrate. The prepared transparent substrate was cleaned with isopropyl alcohol for 5 minutes by using ultrasonic wave, with pure water for 5 minutes, and finally with isopropyl alcohol for 5 minutes by using ultrasonic wave.

The cleaned transparent substrate was fixed to a substrate holder of a commercial apparatus for vacuum vapor deposition (a product of NIPPON SHINKU GIJUTU Co., Ltd.). HI-3 obtained in Example 1 was placed into an electrically heated boat made of molybdenum, and HT-23 obtained in Preparation Example 1 was placed into another electrically heated boat made of molybdenum. DPVBi obtained in Preparation Example 3 was placed into still another electrically heated boat made of molybdenum. The pressure in the vacuum chamber was then reduced to $1\times10^{-3}$ Pa. On the substrate, HI-3, HT-23, and DPVBi were successively laminated by deposition to the thickness of 60 nm, 23 nm, and 40 nm, respectively, by heating the respective boats successively.

The pressure of the apparatus was then adjusted to an atmospheric pressure, and tris(8-hydroxyquinoline) aluminum (Alq, a product of DOJIN KAGAKU KENKYUSHO Co., Ltd.) was placed in another electrically heated boat made of molybdenum. Magnesium ribbon was placed in still another electrically heated boat made of molybdenum, and silver was placed in a basket made of tungsten. After the pressure in the apparatus was reduced to $2\times10^{-4}$ Pa, the boat containing Alq was first electrically heated to deposit Alq on DPVBi to the thickness of 20 nm. Then, magnesium and silver were vaporized in such amounts that the ratio by weight of magnesium to silver was 10:1 to form a cathode of an alloy of magnesium and silver to the thickness of 200 nm. Thus, an organic electroluminescence device was prepared.

A voltage was applied to the prepared device by connecting the ITO electrode of the device to a positive electrode (+) and the cathode made of the magnesium-silver alloy to a negative electrode (−), and the device was brought to emit light. The following result was obtained by application of the voltage of 8 V: the density of electric current: 1.6 mA/cm$^2$, the luminance: 30 cd/m$^2$, and the efficiency of light emission: 0.74 lumen/W. The prepared device showed a high efficiency.

EXAMPLE 5

An organic electroluminescence device was prepared in accordance with the same procedures as those conducted in Example 4 except that HI-16 obtained in Example 2 was used in place of HI-3 used in Example 4.

A voltage was applied to the prepared device by connecting the ITO electrode of the device to a positive electrode (+) and the cathode made of the magnesium-silver alloy to a negative electrode (−), and the device was brought to emit light. The following result was obtained by application of the voltage of 8 V: the density of electric current: 2.0 mA/cm$^2$, the luminance: 55 cd/m$^2$, and the efficiency of light emission: 1.1 lumen/W. The prepared device showed a high efficiency.

EXAMPLE 6

An organic electroluminescence device was prepared in accordance with the same procedures as those conducted in Example 4 except that HI-35 obtained in Example 3 was used in place of HI-3 used in Example 4.

A voltage was applied to the prepared device by connecting the ITO electrode of the device to a positive electrode (+) and the cathode made of the magnesium-silver alloy to a negative electrode (−), and the device was brought to emit light. The following result was obtained by application of the voltage of 8 V: the density of electric current: 1.8 mA/cm$^2$, the luminance: 40 cd/m$^2$, and the efficiency of light emission: 0.87 lumen/W. The prepared device showed a high efficiency.

EXAMPLE 7

An organic electroluminescence device was prepared in accordance with the same procedures as those conducted in Example 4 except that HT-39 obtained in Preparation Example 2 was used in place of HT-23 used in Example 4.

A voltage was applied to the prepared device by connecting the ITO electrode of the device to a positive electrode (+) and the cathode made of the magnesium-silver alloy to a negative electrode (−), and the device was brought to emit light. The following result was obtained by application of the voltage of 8 V: the density of electric current: 2.1 4 mA/cm², the luminance: 38 cd/m², and the efficiency of light emission: 0.71 lumen/W. The prepared device showed a high efficiency.

Comparative Example 1

An organic electroluminescence device was prepared in accordance with the same procedures as those conducted in Example 4 except that MTDATA obtained in Preparation Example 4 was used in place of HI-3 used in Example 4.

A voltage was applied to the prepared device by connecting the ITO electrode of the device to a positive electrode (+) and the cathode made of the magnesium-silver alloy to a negative electrode (−), and the device was brought to emit light. The following result was obtained by application of the voltage of 8 V: the density of electric current: 2.1 mA/cm², the luminance: 20 cd/m², and the efficiency of light emission: 0.37 lumen/W. The prepared device showed a low efficiency.

MTDATA

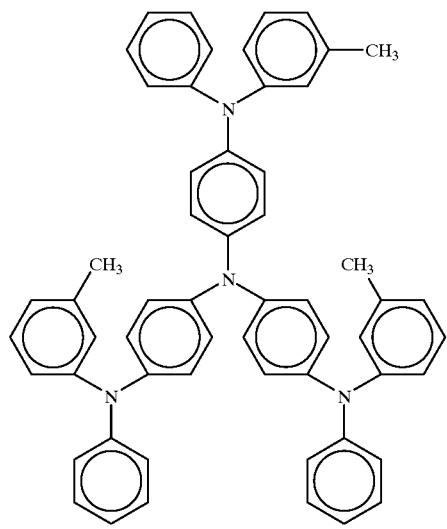

Comparative Example 2

An organic electroluminescence device was prepared in accordance with the same procedures as those conducted in Example 4 except that HT-23 was not laminated.

A voltage was applied to the prepared device by connecting the ITO electrode of the prepared device to a positive electrode (+) and the cathode made of the magnesium-silver alloy to a negative electrode (−), and the device was brought to emit light. The following result was obtained by application of the voltage of 8 V: the density of electric current: 7.0 mA/cm², the luminance: 6.0 cd/m², and the efficiency of light emission: 0.03 lumen/W. The prepared device showed a low efficiency.

Comparative Example 3

An organic electroluminescence device was prepared in accordance with the same procedures as those conducted in Example 4 except that TA-1 obtained in Preparation Example 5 was used in place of HI-3 used in Example 4.

A voltage was applied to the prepared device by connecting the ITO electrode of the prepared device to a positive electrode (+) and the cathode made of the magnesium-silver alloy to a negative electrode (−), and the device was brought to emit light, The following result was obtained by application of the voltage of 8 V: the density of electric current: 1.5 mA/cm², the luminance: 7.0 cd/m², and the efficiency of light emission: 0.18 lumen/W. The prepared device showed a low efficiency.

TA-1:

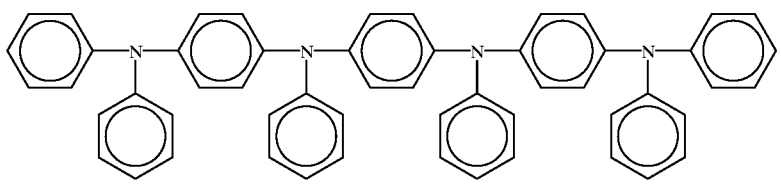

Comparative Example 4

An organic electroluminescence device was prepared in accordance with the same procedures as those conducted in Example 4 except that BTBIBT was used in place of HI-3 used in Example 4, and DMOVCH was used in place of HT-23 used in Example 4.

A voltage was applied to the prepared device by connecting the ITO electrode of the prepared device to a positive electrode (+) and the cathode made of the magnesium-silver alloy to a negative electrode (−), and the device was brought to emit light. The following result was obtained by application of the voltage of 8 V: the density of electric current: 1.9 mA/cm$^2$, the luminance: 17 cd/m$^2$, and the efficiency of light emission: 0.35 lumen/W. The prepared device showed a low efficiency.

As shown in the above, the organic thin film of the present invention had a very excellent property for the electronic photography.

As shown in the above results, the organic electroluminescence devices in Comparative Examples 1 to 4 which had constitutions based on the conventional technology showed efficiencies of light emission as low as 0.03 to 0.37 lumen/W. In contrast, as shown in Examples 4 to 7, the organic electroluminescence devices having the constitution of the present invention showed remarkably increased efficiencies of light emission which were as high as 0.71 to 1.1 lumen/W. As clearly shown in Example 8, the organic thin film of the present invention showed excellent hole injecting and transporting properties.

BTBIBT:

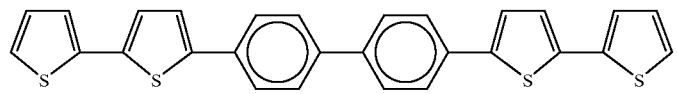

DMOVCH:

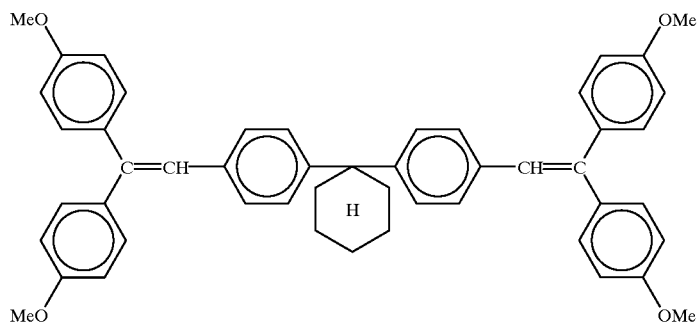

EXAMPLE 8

On an aluminum substrate, an undercoat layer comprising a methoxymethylated nylon (a product of UNITIKA Co., Ltd.; trade name, T-8) was formed to the thickness of 0.1 μm. On the formed undercoat layer, a layer for charge generation comprising an A-type titanylphthalocyanine and polyvinylbutyral (a product of SEKISUI KAGAKU Co., Ltd.; trade name, BX-1) was formed to the thickness of 0.1 μm. On the thus formed layer for charge generation, a hole injecting thin film was formed by depositing HI-3 obtained in Example 1 and HT-23 obtained in Preparation Example 1 to the thickness of 60 nm and 20 nm, respectively, by the vacuum vapor deposition in accordance with the same procedures as those conducted in Example 4.

The property for the electronic photography of this film was evaluated by using a testing apparatus for electrostatic recording produced by KAWAGUCHI DENKI Co., Ltd. in the following manner. The film was charged by corona discharge of −6 kV, and the charge was then attenuated in the dark for 3 seconds. The film was then exposed to white light of 5 luxes for 5 seconds, and the time (by second) passed before the surface potential of the film reached ½ of the initial value was obtained. As the result, the half-life light exposure was found to be 0.4 lux-second.

EXAMPLE 9

Preparation of Compound (3)

(1) Synthesis of 4,4′-diamino-4″-phenyl-triphenylamine (Compound A)

Into a 500 ml flask of an egg plant shape, 25 g of 4-aminobiphenyl (a product of ALDRICH Co.), 62.6 g of 4-fluoronitrobenzene (a product of HIROSHIMA WAKO Co., Ltd.), 0.94 g of copper powder, 40.8 g of anhydrous potassium carbonate, and 280 ml of dimethylformamide (DMF; a product of HIROSHIMA WAKO Co., Ltd.) were placed. The resultant mixture was heated to 160° C. in an oil bath under an argon stream, and the reaction was allowed to proceed in this mixture at this temperature for 72 hours. After the reaction had been completed, the insoluble portion was removed from the reaction product by filtration, and DMF was removed from the filtrate by distillation. To the residual product, 1.5 liters of methanol was added, and the resultant mixture was stirred under heating at 60° C. The formed crystal was separated by filtration. After this procedure was repeated 4 times, 33.8 g of 4,4′-dinitro-4″-phenyl-triphenylamine was obtained.

Into a 1 liter flask of an egg plant shape, 4,4′-dinitro-4″-phenyl-triphenylamine obtained above, 500 ml of DMF, and 6.8 g of a 5% by weight Pd—C (a product of HIROSHIMA WAKO Co., Ltd.) were placed. Then, hydrogen gas was blown into the obtained mixture under an atmospheric pressure to allow the hydrogenation reaction to proceed at a room temperature. After the reaction had been completed, the catalyst was removed from the reaction product by filtration. The resultant reaction solution was poured into 1.5 liters of water, and the precipitated crystal was separated by filtration. The obtained crystal was extracted with 1 liter of ethyl acetate. The obtained extract was washed with water and dehydrated with anhydrous magnesium sulfate (a product of HIROSHIMA WAKO Co., Ltd.), and the solvent was removed from the dehydrated extract to obtain 25 g of the compound of the object: 4,4'-diamino-4"-phenyl-triphenylamine (Compound A).

(2) Synthesis of Compound (3)

Into a 500 flask of an egg plant shape, 5.01 g of 4,4'-diamino-4"-phenyl-triphenylamine (Compound A) obtained above in (1), 25 ml of 3-iodotoluene (a product of HIROSHIMA WAKO Co., Ltd.), 16 g of anhydrous potassium carbonate, 6 g of copper powder, and 200 ml of dimethylsulfoxide (DMSO; a product of HIROSHIMA WAKO Co., Ltd.) were placed, and the reaction was allowed to proceed in the resultant mixture under an argon stream at 180° C. for 6 hours. After the reaction was completed, the insoluble portion was removed from the reaction product by filtration, and the obtained filtrate was extracted with 1 liter of methylene chloride. The extract was washed with water and dehydrated with anhydrous magnesium sulfate, and the solvent was removed from the dehydrated extract. The obtained product was purified by using a column packed with activated alumina (a product of HIROSHIMA WAKO Co., Ltd.) to obtain 6.5 g of a light yellow powder.

This product was identified as 4,4'-bis[N,N-di-(3-tolyl)amino]-4"-phenyl-triphenylamine by the measurements of the field diffusion mass spectrum (FD-MS) and the proton nuclear magnetic resonance spectrum ($^1$H-NMR). The yield was 63% (based on Compound A), and the melting point was 180 to 181° C.

Figure 2:
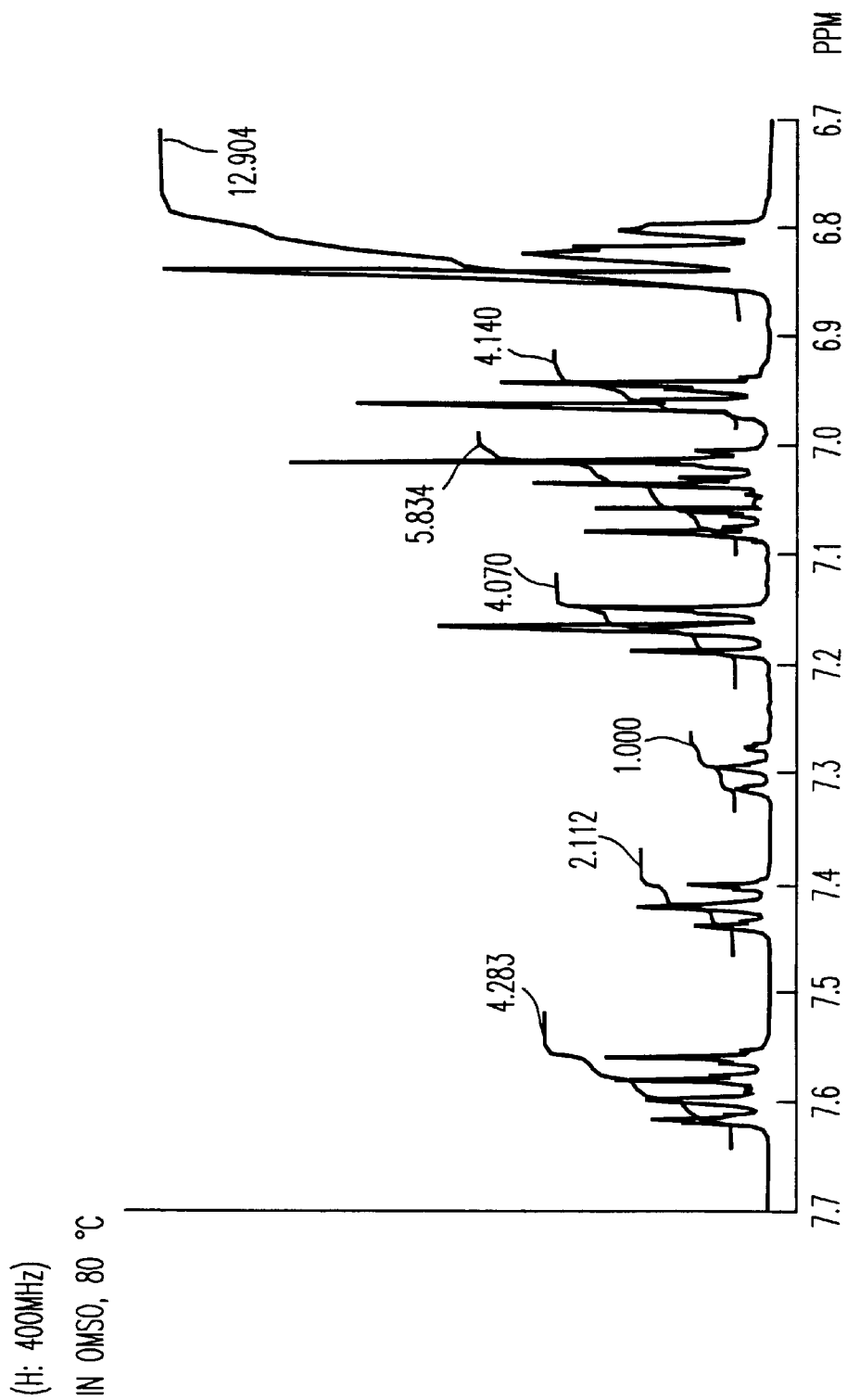
FIG. 2 shows an enlarged detail of a part of the $^1$H-NMR spectrum if 4,4'-bis[N,N-di-(3-tolyl)amino]-4"-phenyl-triphenylamine obtained in Example 9.

The whole chart of the $^1$H-NMR is shown in FIG. 1, and the enlarged detail of the $^1$H-NMR is shown in FIG. 2.

In the measurement of FD-MS of this compound, the main peak was observed at m/z=711, and this corresponds to $C_{52}H_{45}N_3$=711.

EXAMPLE 10
Preparation of Compound (20)

The same procedures as those conducted in Example 9 were conducted except that 25 ml of 4-iodoanisol (a product of HIROSHIMA WAKO Co., Ltd.) was used in place of 3-iodotoluene used in Example 9 (2), and 5.75 g of 4,4'-bis[N,N-di(4-anisyl)amino]-4"-phenyl-triphenylamine was obtained. The yield was 52% (based on Compound A), and the melting point was 201° C.

The result of the measurement of $^1$H-NMR of this compound is shown in the following:

DMSO-$d_6$: δ7.63~7.55 (dd, 4H); 7.44~7.40 (t, 2H), 7.32~7.28 (t, 1H); 7.09~7.06 (d, 2H); 7.04~6.94 (dd, 8H); 6.81~6.40 (dd, 16H); 3.72 (s, 12H) ppm.

EXAMPLE 11
Preparation of Compound (36)

The same procedures as those conducted in Example 9 were conducted except that 35 g of 4-iodobiphenyl obtained in Example 3 (1) was used in place of 3-iodotoluene used in Example 9 (2), and 4.65 g of 4,4'-bis[N,N-di-(biphenyl)amino]-4"-phenyl-triphenylamine was obtained. The yield was 34% (based on Compound A), and the melting point was 277° C.

The result of the measurement of $^1$H-NMR of this compound is shown in the following:

DMSO-$d_6$: δ7.63~7.55 (dd, 20H); 7.45~7.39 (t, 10H), 7.32~7.27 (t, 5H); 7.09~7.06 (d, 10H); 7.04~6.94 (dd, 8H) ppm.

EXAMPLE 12
Preparation of Compound (43)

(1) Synthesis of 4,4'-diamino-4"-(4-tolyl)-triphenylamine (Compound B)

A mixture of 100 g of phenyltoluene (a product of ALDRICH Co.) and 1 liter of acetic acid was heated to 80° C., and 200 ml of fuming nitric acid was added dropwise to the heated mixture at 75 to 90° C. during 2 hours. After the resultant mixture was kept being stirred for 1 hour at this temperature, the mixture was cooled to 50° C., and 1 liter of methanol was added to the cooled mixture to obtain 47 g of a crystal. The obtained crystal was dissolved in 1 liter of DMF. To the resultant solution, 10 g of a 5% Pd—C was added, and the hydrogenation was conducted under an atmospheric pressure for 6 hours by bubbling hydrogen gas through the reaction mixture.

The insoluble portion was then removed from the reaction mixture by filtration, and the obtained filtrate was poured into 3 liters of water saturated with sodium chloride. The precipitated crystal was separated by filtration and reprecipitated by using 500 ml of toluene to obtain 37 g of 4'-methyl-4-aminobiphenyl.

Then, the same procedures as those conducted in Example 9 (1) were conducted except that 25 g of 4'-methyl-4-aminobiphenyl obtained in the above was used in place of 4-aminobiphenyl used in Example 9 (1), and 22 g of 4,4'-diamino-4"-(4-tolyl)-triphenylamine (Compound B) was obtained.

(2) Synthesis of Compound (43)

The same procedures as those conducted in Example 9 (2) were conducted except that 5.00 g of Compound B was used in place of Compound A used in Example 9 (2), and 25 ml of iodobenzene (a product of HIROSHIMA WAKO Co., Ltd.) was used in place of 3-iodotoluene used in Example 9 (2), and 6.24 g of 4,4'-bis(N,N-diphenylamino)-4"-(4-tolyl)triphenylamine was obtained. The yield was 68% (based on Compound B), and the melting point was 171° C.

The result of the measurement of $^1$H-NMR of this compound is shown in the following:

DMSO-$d_6$: δ7.63~7.55 (dd, 4H); 7.53~6.81 (m, 20H); 7.11~7.03 (dd, 4H); 7.04~6.94 (dd, 8H); 2.28 (s, 3H) ppm.

EXAMPLE 13
Preparation of Compound (57)

(1) Synthesis of 4,4'-diamino-4"-(4-anisyl)-triphenylamine (Compound C)

A mixture of 100 g of 4-phenylanisole (a product of ALDRICH Co.) and 1 liter of acetic acid was heated to 80° C., and 200 ml of fuming nitric acid was added dropwise to the heated mixture at 75 to 90° C. during 2 hours. After the resultant mixture was kept being stirred for 1 hour at this temperature, the mixture was cooled to 50° C., and 1 liter of methanol was added to the cooled mixture to obtain 51 g of a crystal.

The obtained crystal was dissolved in 1 liter of DMF. To the resultant solution, 10 g of a 5% Pd—C was added, and the hydrogenation was conducted under an atmospheric pressure for 6 hours by bubbling hydrogen gas through the reaction mixture.

The insoluble portion was removed from the reaction mixture by filtration, and the obtained filtrate was poured into 3 liters of water saturated with sodium chloride. The precipitated crystal was separated by filtration and reprecipitated by using 500 ml of toluene to obtain 41 g of 4'-methoxy-4-aminobiphenyl.

Then, the same procedures as those conducted in Example 9 (1) were conducted except that 25 g of 4'-methoxy-4-aminobiphenyl obtained in the above was used in place of 4-aminobiphenyl used in Example 9 (1), and 23 g of 4,4'-diamino-4"-(4-anisyl)-triphenylamine (Compound C) was obtained.

(2) Synthesis of Compound (57)

The same procedures as those conducted in Example 9 (2) were conducted except that 5.00 g of Compound C was used in place of Compound A used in Example 9 (2), and 25 ml of iodobenzene was used in place of 3-iodotoluene used in Example 9 (2), and 5.58 g of 4,4'-bis(N,N-diphenylamino)-4"-(4-anisyl)-triphenylamine was obtained. The yield was 62% (based on Compound C), and the melting point was 177° C.

The result of the measurement of $^1$H-NMR of this compound is shown in the following:

DMSO-$d_6$: δ7.62~7.55 (dd, 4H); 7.53~6.80 (m, 20H), 7.12~7.02 (dd, 4H); 7.03~6.94 (dd, 8H); 3.70 (s, 3H) ppm.

EXAMPLE 14

Preparation of Compound (70)

(1) Synthesis of 4,4'-diamino-4"-biphenyl-triphenylamine (Compound D)

The same procedures as those conducted in Example 9 (1) were conducted except that 25 g of 4-aminoterphenyl (a product of TOKYO KASEI Co., Ltd.) was used in place of 4-aminobiphenyl used in Example 9 (1), and 14 g of 4,4'-diamino-4"-biphenyl-triphenylamine (Compound D) was obtained.

(2) Preparation of Compound (70)

The same procedures as those conducted in Example 9 (2) were conducted except that 5.00 g of Compound D was used in place of Compound A used in Example 9 (2), and 25 ml of iodobenzene was used in place of 3-iodotoluene used in Example 9 (2), and 3.21 g of 4,4'-bis(N,N-diphenylamino)-4"-biphenyl-triphenylamine was obtained. The yield was 38% (based on Compound D), and the melting point was 178° C.

The result of the measurement of $^1$H-NMR of this compound is shown in the following:

DMSO-$d_6$: δ7.62~7.55 (dd, 4H); 7.52~6.81 (m, 20H), 7.42~7.38 (t,2H); 7.31~7.27 (t, 1H); 7.08~7.00 (dd, 4H); 7.09~7.06 (dd, 4 H); 7.04~6.94 (dd, 8H) ppm.

EXAMPLE 15

Preparation of an Organic Electroluminescence Device by Using Compound (3)

On a glass substrate having the size of 25 mm×75 mm×1.1 mm, an ITO (indium tin oxides) electrode was formed to the thickness of 100 nm, and the obtained product was used as the transparent substrate. The prepared transparent substrate was cleaned with isopropyl alcohol for 5 minutes by using ultrasonic wave, with pure water for 5 minutes, and finally with isopropyl alcohol for 5 minutes by using ultrasonic wave.

The cleaned transparent substrate was fixed to a substrate holder of a commercial apparatus for vacuum vapor deposition (a product of NIPPON SHINKU GIJUTU Co., Ltd.). Into 5 electrically heated boats made of molybdenum, the following compounds were separately placed: 500 mg of Compound (3), 200 mg of N,N'-diphenyl-N,N'-bis(3-methylphenyl)-[1,1'-biphenyl]-4,4'-diamine (TPD), 200 mg of 4,4'-bis(2,2-diphenylvinyl)biphenyl (DPVBi), 200 mg of 4,4'-bis[2-(4-(N,N-diphenylamino)phenyl)vinyl]biphenyl (DPAVBi), and 100 mg of tris(8-hydroxyquinoline) aluminum (Alq).

After the pressure in the apparatus was reduced to $2\times10^{-4}$ Pa, the boat containing Compound (3) was heated to deposit Compound (3) on the substrate, and a hole injecting layer having the thickness of 60 nm was formed. Then, the boat containing TPD was heated to vaporize TPD, and a hole transporting layer having the thickness of 40 nm was formed. As the next step, the boats containing DPVBi and DPAVBi were simultaneously heated to vaporize DPVBi and DPAVBi, and a mixed light emitting layer having the thickness of 40 nm was formed by the vapor deposition on the hole transporting layer [the ratio of the two mixed components was as follows: DPVBi:DPAVBi=40:1 (ratio by weight)]. As the final step, the boat containing Alq was heated to deposit Alq on the light emitting layer, and an electron injecting layer having the thickness of 20 nm was formed.

Then, the product obtained above was taken out of the vacuum chamber, and a mask made of stainless steel was placed on the above electron injecting layer. The combined product was fixed again to the substrate holder. Into a basket made of tungsten, 0.5 g of silver wire was placed, and 1 g of magnesium ribbon was placed into another boat made of tungsten. The pressure in the vacuum chamber was then reduced to $1\times10^{-4}$ Pa, and magnesium and silver were vapor deposited simultaneously at the rates of vapor deposition of 1.8 nm/sec and 0.1 nm/sec, respectively, to prepare a mixed electrode of magnesium and silver.

The voltage of 8 V was applied to the obtained device by connecting the ITO electrode of the prepared device to a positive electrode (+) and the cathode made of the magnesium-silver alloy to a negative electrode (−) to test emission of light, and a uniform light of blue color was obtained. The following initial properties were obtained by application of the voltage of 8 V: the density of electric current: 3.9 mA/cm$^2$, the luminance: 170 cd/m$^2$, and the efficiency of light emission: 1.71 lumen/W. When the initial luminance was adjusted to 100 cd/m$^2$, and the device was continuously driven at a constant electric current under a dry nitrogen, the half-life time (the time before the luminance reaches one half of the initial value) was found to be 1500 hours.

Comparative Example 5

An organic electroluminescence device was prepared in accordance with the same procedures as those conducted in Example 15 except that 4,4',4"-tris(3- methylphenylphenylamino)triphenylamine (MTDATA, the compound described in the specification of Japanese Patent Application Laid-Open No. Heisei 4(1992)-308688) was used for the hole injecting layer in place of Compound (3) used in Example 15.

The voltage of 8 V was applied to the obtained device in accordance with the same method as that used in Example 15 to test emission of light, and a uniform light of blue color was obtained. The following initial properties were obtained by application of the voltage of 8 V: the density of electric current: 4.0 mA/cm$^2$, the luminance: 140 cd/m$^2$, and the efficiency of light emission: 1.37 lumen/W. When the initial luminance was adjusted to 100 cd/m$^2$, and the device was continuously driven at a constant electric current under a dry nitrogen, the half-life time was found to be 800 hours. This device had a life clearly inferior to that of the device prepared in Example 15.

EXAMPLE 16

An organic electroluminescence device was prepared in accordance with the same procedures as those conducted in Example 15 except that Compound (20) was used in place of Compound (3) used in Example 15.

The test of emission of light was conducted in accordance with the same method as that used in Example 15, and the following initial properties were obtained by application of the voltage of 8 V: the density of electric current: 4.2 mA/cm$^2$, the luminance: 172 cd/m$^2$, and the efficiency of light emission: 1.61 lumen/W. When the initial luminance was adjusted to 100 cd/m$^2$, and the device was continuously driven at a constant electric current under a dry nitrogen, the half-life time was found to be 1300 hours.

EXAMPLE 17

An organic electroluminescence device was prepared in accordance with the same procedures as those conducted in Example 15 except that Compound (36) was used in place of Compound (3) used in Example 15.

The test of emission of light was conducted in accordance with the same method as that used in Example 15, and the following initial properties were obtained by application of the voltage of 8 V: the density of electric current: 4.0 mA/cm$^2$, the luminance: 168 cd/m$^2$, and the efficiency of light emission: 1.65 lumen/W. When the initial luminance was adjusted to 100 cd/m$^2$, and the device was continuously driven at a constant electric current under a dry nitrogen, the half-life time was found to be 1400 hours.

EXAMPLE 18

An organic electroluminescence device was prepared in accordance with the same procedures as those conducted in Example 15 except that Compound (43) was used in place of Compound (3) used in Example 15.

The test of emission of light was conducted in accordance with the same method as that used in Example 15, and the following initial properties were obtained by application of the voltage of 8 V: the density of electric current: 4.0 mA/cm$^2$, the luminance: 170 cdlm$^2$, and the efficiency of light emission: 1.71 lumen/W. When the initial luminance was adjusted to 100 cd/m$^2$, and the device was continuously driven at a constant electric current under a dry nitrogen, the half-life time was found to be 1500 hours.

EXAMPLE 19

An organic electroluminescence device was prepared in accordance with the same procedures as those conducted in Example 15 except that Compound (57) was used in place of Compound (3) used in Example 15.

The test of emission of light was conducted in accordance with the same method as that used in Example 15, and the following initial properties were obtained by application of the voltage of 8 V: the density of electric current: 4.1 mA/cm$^2$, the luminance: 167 cd/m$^2$, and the efficiency of light emission: 1.60 lumen/W. When the initial luminance was adjusted to 100 cd/m$^2$, and the device was continuously driven at a constant electric current under a dry nitrogen, the half-life time was found to be 1400 hours.

EXAMPLE 20

An organic electroluminescence device was prepared in accordance with the same procedures as those conducted in Example 15 except that Compound (70) was used in place of Compound (3) used in Example 15.

The test of emission of light was conducted in accordance with the same method as that used in Example 15, and the following initial properties were obtained by application of the voltage of 8 V: the density of electric current: 3.9 mA/cm$^2$, the luminance: 157 cd/m$^2$, and the efficiency of light emission: 1.58 lumen/W. When the initial luminance was adjusted to 100 cd/m$^2$, and the device was continuously driven at a constant electric current under a dry nitrogen, the half-life time was found to be 1300 hours.

INDUSTRIAL APPLICABILITY

As described in the above, the organic electroluminescence device of the present invention has little possibility of dielectric breakdown after storage for a long time, shows a remarkably high efficiency of light emission, and is advantageously used as a light emitting device in various types of display apparatus.

The thin film of the present invention shows very excellent hole injecting and transporting properties and is advantageously used for organic electroluminescence devices as well as other organic devices and photosensitive films in the electronic photography.

The triamine compound of the present invention is a novel compound and provides an organic electroluminescence device having a long life and showing an excellent stability of light emission when the triamine compound is used for the device.

We claim:

1. An organic electroluminescence device which comprises an organic layer at least comprising a layer of a hole transporting zone and a layer of a light emitting zone and a pair of electrodes disposed on both sides of the organic layer, wherein the layer of a hole transporting zone at least comprises a hole injecting layer and a hole transporting layer, and the hole injecting layer contains a compound represented by general formula (I):

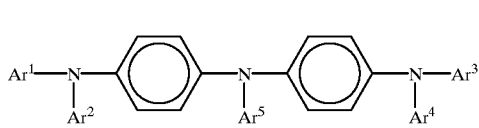

wherein $Ar^1$ to $Ar^5$ represent each an aryl group having 6 to 18 core carbon atoms which is unsubstituted or substituted with an alkyl group, an alkoxy group, vinyl group, or styryl group, and may be the same with each other or different from each other and is in contact with an anode.

2. An organic electroluminescence device according to claim 1, wherein $Ar^1$ to $Ar^5$ in general formula (I) represent each an aryl group having 6 to 18 carbon atoms which is unsubstituted or substituted with an alkyl group, an alkoxy group, vinyl group, or styryl group.

3. An organic electroluminescence device according to claim 1, wherein the hole transporting layer contains a compound represented by general formula (II):

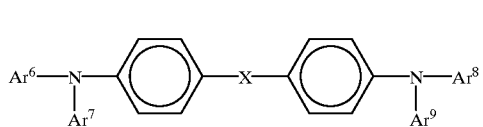

wherein X represents a single bond, methylene group, phenylene group, biphenylene group, —O—, —S—, or a group represented by any of:

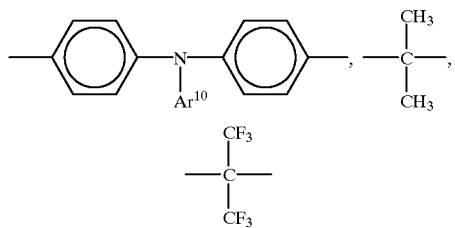

and $Ar^6$ to $Ar^{10}$ represent each an aryl group having 6 to 18 core carbon atoms which is unsubstituted or substituted with an alkyl group, an alkoxy group, vinyl group, or styryl group, and may be the same with each other or different from each other.

4. An organic electroluminescence device according to claim 3, wherein $Ar^6$ to $Ar^{10}$ in general formula (II) represent each an aryl group having 6 to 18 carbon atoms which is unsubstituted or substituted with an alkyl group, an alkoxy group, vinyl group, or styryl group.

5. An organic electroluminescence device according to claim 1, wherein the hole injecting layer and the hole transporting layer have each a thickness of 5 nm to 5 μm.

6. An organic electroluminescence device according to claim 3, wherein the hole injecting layer and the hole transporting layer have each a thickness of 5 nm to 5 μm.

7. An organic thin film comprising two layers which are a layer containing a compound represented by general formula (I) and having a thickness of 5 nm to 5 μm and a layer containing a compound represented by general formula (II) and having a thickness of 5 nm to 5 μm wherein general formula (I) is as follows:

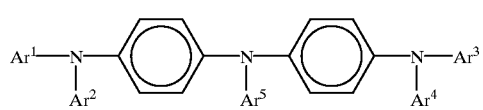

where $Ar^1$ to $Ar^5$ represent each an aryl group having 6 to 18 core carbon atoms which is unsubstituted or substituted with an alkyl group, an alkoxy group, vinyl group, or styryl group, and may be the same with each other or different from each other;

and wherein general formula (II) is:

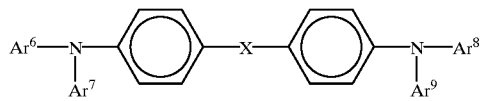

where X represents a single bond, methylene group, phenylene group, biphenylene group, —O—, —S—, or a group represented by any of:

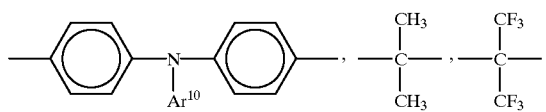

and $Ar^6$ to $A^{10}$ represent each an aryl group having 6 to 18 core carbon atoms which is unsubstituted or substituted with an alkyl group, an alkoxy group, vinyl group, or styryl groups, and may be the same with each other or different from each other.

8. A triamine compound represented by general formula (III):

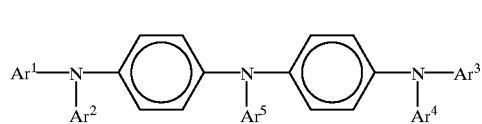

wherein $Ar^1$ to $Ar^4$ represent each an aryl group having 6 to 18 core carbon atoms which is unsubstituted or substituted with an alkyl group, an alkoxy group, vinyl group, or styryl group and may be the same with each other or different from each other, and $Ar^5$ represents biphenyl group which is unsubstituted or substituted.

9. A triamine compound according to claim 8, wherein $Ar^5$ in general formula (III) represents an aryl group represented by:

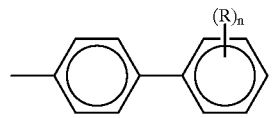

wherein R represents hydrogen, an alkyl group having 1 to 6 carbon atoms, an alkoxy group having 1 to 6 carbon atoms, or phenyl group, n represents an integer of 0 to 5, and when a plurality of R are present, the plurality of R may be the same with each other or different from each other, and $Ar^1$ to $Ar^4$ represent each an aryl group represented by any of:

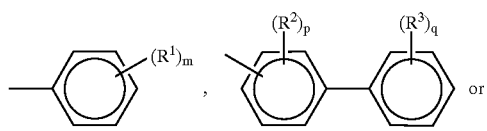

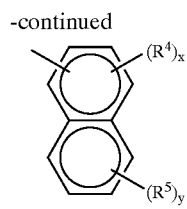

wherein $R^1$ to $R^5$ represent each hydrogen, an alkyl group having 1 to 6 carbon atoms, an alkoxy group having 1 to 6 carbon atoms, or phenyl group, m represents an integer of 0 to 5, p represents an integer of 0 to 4, q represents an integer of 0 to 5, x represents an integer of 0 to 3, y represents an integer of 0 to 4, and when a plurality of $R^1$, $R^2$, $R^3$, $R^4$, or $R^5$ are present, the plurality of $R^1$, $R^2$, $R^3$, $R^4$, or $R^5$ may be the same with each other or different from each other.

10. The hole transporting layer of claim 3, wherein said compound represented by general formula (II) is:

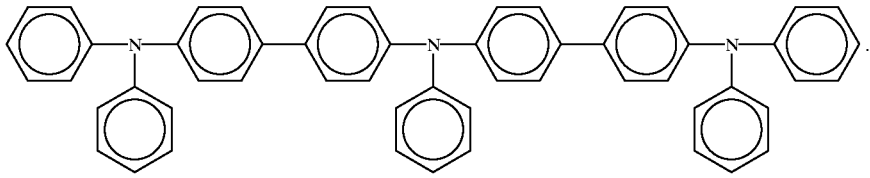

* * * * *